US012805712B2

(12) United States Patent
Zhang

(10) Patent No.: US 12,805,712 B2
(45) Date of Patent: Nov. 24, 2026

(54) SINGLE USE ENDOSCOPES, CANNULAS, AND OBTURATORS WITH INTEGRATED VISION AND ILLUMINATION

(71) Applicant: Noah Medical Corporation, Redwood City, CA (US)

(72) Inventor: Jian Zhang, Redwood City, CA (US)

(73) Assignee: Noah Medical Corporation, San Carlos, CA (US)

( * ) Notice: Subject to any disclaimer, the term of this patent is extended or adjusted under 35 U.S.C. 154(b) by 600 days.

(21) Appl. No.: 17/630,503

(22) PCT Filed: Mar. 3, 2020

(86) PCT No.: PCT/US2020/020819
§ 371 (c)(1),
(2) Date: Jan. 26, 2022

(87) PCT Pub. No.: WO2020/180879
PCT Pub. Date: Sep. 10, 2020

(65) Prior Publication Data

US 2022/0240760 A1 Aug. 4, 2022

Related U.S. Application Data

(60) Provisional application No. 62/814,295, filed on Mar. 6, 2019.

(51) Int. Cl.
*A61B 1/06* (2006.01)
*A61B 1/00* (2006.01)
(Continued)

(52) U.S. Cl.
CPC ........ *A61B 1/0684* (2013.01); *A61B 1/00016* (2013.01); *A61B 1/00032* (2013.01);
(Continued)

(58) Field of Classification Search
CPC ............ A61B 1/00016; A61B 1/00032; A61B 1/00103; A61B 1/00124; A61B 1/00126;
(Continued)

(56) References Cited

U.S. PATENT DOCUMENTS 5,569,292 A * 10/1996 Scwemberger .... A61B 17/3417
600/101
5,609,562 A * 3/1997 Kaali .................. A61B 1/3132
604/164.08
(Continued)

FOREIGN PATENT DOCUMENTS

CN 101188966 A 5/2008
CN 107802230 A 3/2018
(Continued)

OTHER PUBLICATIONS

EP20766047.3 Search Report and Opinion dated Nov. 8, 2022.
(Continued)

*Primary Examiner* — Anhtuan T Nguyen
*Assistant Examiner* — Li-Ting Song
(74) *Attorney, Agent, or Firm* — Wilson Sonsini Goodrich & Rosati

(57) ABSTRACT

A surgical port placement device with integrated vision and illumination is provided. The surgical port placement device comprises: a cannula, a hand piece connected with to cannula, an obturator inserted into the cannula, a camera and an illumination element residing at the distal end of the port placement device.

8 Claims, 20 Drawing Sheets

(51) Int. Cl.

| | |
|---|---|
| ***A61B 1/005*** | (2006.01) |
| ***A61B 1/018*** | (2006.01) |
| ***A61B 1/05*** | (2006.01) |
| ***A61B 1/07*** | (2006.01) |
| ***A61B 1/313*** | (2006.01) |
| ***A61B 46/10*** | (2016.01) |

(52) U.S. Cl.
CPC ........ *A61B 1/0008* (2013.01); *A61B 1/00103* (2013.01); *A61B 1/00124* (2013.01); *A61B 1/00126* (2013.01); *A61B 1/00128* (2013.01); *A61B 1/0052* (2013.01); *A61B 1/0057* (2013.01); *A61B 1/018* (2013.01); *A61B 1/05* (2013.01); *A61B 1/06* (2013.01); *A61B 1/07* (2013.01); *A61B 1/313* (2013.01); *A61B 46/10* (2016.02)

(58) Field of Classification Search
CPC . A61B 1/00128; A61B 1/0052; A61B 1/0057; A61B 1/018; A61B 1/05; A61B 1/07; A61B 1/313; A61B 46/10; A61B 1/012; A61B 1/015; A61B 1/00066; A61B 17/34; A61B 1/00142–00144
See application file for complete search history.

(56) References Cited

U.S. PATENT DOCUMENTS

| | | | | |
|---|---|---|---|---|
| 5,658,236 | A * | 8/1997 | Sauer | A61B 17/3417 600/105 |
| 5,860,996 | A * | 1/1999 | Urban | A61B 17/3496 604/264 |
| 6,387,043 | B1 * | 5/2002 | Yoon | A61B 1/05 600/129 |
| 7,862,504 | B2 | 1/2011 | Kura et al. | |
| 8,608,652 | B2 | 12/2013 | Voegele et al. | |
| 10,110,785 | B2 | 10/2018 | Hoeg et al. | |
| 10,813,536 | B2 * | 10/2020 | Fischvogt | A61B 1/313 |
| 2003/0097043 | A1 * | 5/2003 | Ouchi | A61B 1/00142 600/122 |
| 2005/0288622 | A1 * | 12/2005 | Albrecht | A61M 13/003 604/23 |
| 2006/0149129 | A1 | 7/2006 | Watts et al. | |
| 2007/0043264 | A1 | 2/2007 | Gillis et al. | |
| 2009/0048486 | A1 | 2/2009 | Surti | |
| 2010/0016664 | A1 * | 1/2010 | Viola | A61B 17/3423 600/114 |
| 2013/0109919 | A1 * | 5/2013 | Sugiyama | A61B 1/00006 600/117 |
| 2013/0197309 | A1 * | 8/2013 | Sakata | A61B 1/00128 600/132 |
| 2014/0275771 | A1 * | 9/2014 | Henley | A61B 1/00179 600/104 |
| 2015/0351794 | A1 * | 12/2015 | Mastri | A61B 17/3474 600/204 |
| 2016/0022146 | A1 * | 1/2016 | Piron | A61B 5/0059 600/411 |
| 2016/0278738 | A1 * | 9/2016 | Buchalter | A61B 8/4422 |
| 2016/0302653 | A1 * | 10/2016 | Inoue | G01C 3/08 |
| 2016/0309995 | A1 | 10/2016 | Intoccia, Jr. et al. | |
| 2016/0345816 | A1 * | 12/2016 | Hamel | A61B 17/3417 |
| 2016/0353969 | A1 * | 12/2016 | Kikuchi | A61B 34/20 |
| 2017/0078583 | A1 * | 3/2017 | Haggerty | H04N 23/55 |
| 2017/0238962 | A1 * | 8/2017 | Hansen | A61B 90/37 |
| 2017/0307872 | A1 * | 10/2017 | Hatase | H04N 23/51 |
| 2017/0332912 | A1 * | 11/2017 | Tsukashima | A61B 5/4064 |
| 2017/0360288 | A1 * | 12/2017 | Kirn | A61B 1/0684 |
| 2018/0161024 | A1 * | 6/2018 | Davis | A61B 1/00 |
| 2019/0117259 | A1 * | 4/2019 | Forsberg | A61B 17/3468 |
| 2019/0175007 | A1 * | 6/2019 | Sørensen | A61B 1/00117 |
| 2019/0246873 | A1 * | 8/2019 | Lu | A61B 1/307 |
| 2019/0290321 | A1 * | 9/2019 | Zhu | A61B 17/3478 |
| 2019/0298407 | A1 * | 10/2019 | Olsen | A61B 17/3472 |
| 2020/0397224 | A1 * | 12/2020 | Mirza | A61B 1/00016 |
| 2021/0015347 | A1 * | 1/2021 | Titus | A61B 1/00148 |
| 2021/0220014 | A1 * | 7/2021 | Gitelis | A61B 1/0661 |
| 2022/0378279 | A1 * | 12/2022 | Poll | A61B 1/00179 |
| 2023/0076439 | A1 * | 3/2023 | Zhang | A61B 1/0055 |
| 2024/0156330 | A1 * | 5/2024 | Berg | A61B 50/33 |
| 2025/0025211 | A1 * | 1/2025 | Einarsson | A61B 1/00096 |

FOREIGN PATENT DOCUMENTS

| | | | | |
|---|---|---|---|---|
| DE | 202011052047 | U1 * | 3/2012 | A61B 1/002 |
| GB | 1034222 | A | 6/1966 | |
| WO | WO-2009116969 | A1 | 9/2009 | |
| WO | WO-2011072098 | A2 | 6/2011 | |
| WO | WO-2017212332 | A1 | 12/2017 | |
| WO | WO-2018088498 | A1 | 5/2018 | |
| WO | WO-2020180879 | A1 | 9/2020 | |

OTHER PUBLICATIONS

PCT/US2020/020819 Search Report and Written Opinion dated Jul. 24, 2020.

EP 20766047.3 European Examination Report dated Jun. 6, 2025.

* cited by examiner

SINGLE USE ENDOSCOPES, CANNULAS, AND OBTURATORS WITH INTEGRATED VISION AND ILLUMINATION

REFERENCE

This application claims the benefit of U.S. Provisional Application No. 62/814,295, filed Mar. 6, 2019, which application is incorporated herein by reference.

BACKGROUND

Endoscopy is used to examine inside the body of a subject. The endoscopy procedure uses an endoscope to examine the interior of a hollow organ or cavity of the body. Unlike many other medical imaging techniques, endoscopes are inserted into the organ directly.

Laparoscopy and thoracoscopy belong to the broader field of endoscopy. Laparoscopic and thoracoscopic surgeries, also called minimally invasive surgery (MIS), bandaid surgery, or keyhole surgery, are modern surgical techniques. They are operations performed in the abdomen, pelvis or chest cavity using small incisions with the aid of a camera. The key element is the use of a laparoscope or thoracoscope, which allows viewing of the affected area, as well as performing the operations.

Endoscopes are usually designed to be re-usable. Due to its complicated structures, those traditional endoscopes are very difficult to clean, dis-infect, or sterilize after each procedure, which may cause incident of infection and cross contamination between patients. In addition, traditional endoscopes are also large in sizes, which require enlarged space to operate.

Moreover, traditional general laparoscopic surgeries, thoracic surgeries or other surgeries may require enlarged space inside the patient body with gas insufflation. These surgeries can be manual procedures, or robotic procedures which may involve utilization of instruments and laparoscope/endoscope in such procedures. Such procedure usually includes a process of creating ports on the patient body for laparoscope and instruments known as "port placement". Port placement is required for many manual surgeries and robotics surgeries. Such procedures usually require creating ports on the patient body in order to pass through instruments and laparoscope so that the doctors can have a direct visualization of the inside organs and tissue of the patient through the laparoscope. In a typical procedure, doctors use trocars including obturators and cannulas to make the initial incision into the patient without vision guidance. Once the first incision is made, the obturator is removed, the cannula is kept at the patient body so that a laparoscope is inserted through the cannula into the inside of the patient body. The purpose of using a laparoscope is to guide the following insertions of obturators and cannulas for other ports. There can be three to five cannulas needed to place instruments, and insertion of cannula under direct visualization is preferred. Normally, doctors manipulate the laparoscope to search for the next desirable entry point of the cannula inside the patient body. This process may be repeated until the three to five cannulas are placed.

However, a laparoscope is designed to be used mainly for the surgical procedure after port placement. For instance, the laparoscope tends to have a long shaft to allow doctors maneuver and control the endoscope outside the patient body. The laparoscope may also have high-performance cameras with lens which can be expensive. Such complex structure, complicated components or large dimension and size may not be suitable for port placement procedures.

SUMMARY

Recognized herein is a need for a port placement device. In particular, the present disclosure provides a low-cost, single use port placement endoscope. The endoscope may be integrated with cannula or obturator for general surgeries, thoracic surgeries and various applications. Additionally, the present disclosure provides a miniaturized, low-cost single use articulatable endoscope for diagnosis and treatment by providing compact vision, illumination and structural design of the present disclosure. In some embodiments, the endoscope of the present disclosure may be a miniaturized low-cost port placement device that is integrated with imaging and illumination for operations such as laparoscopic and thoracic surgeries and various other applications.

In one aspect, provided is a miniaturized single use endoscope comprising a distal tip, a shaft, a neck portion connecting the distal tip and the shaft, a proximal end, a camera and an illumination element residing at the distal end of the distal tip, and an overall diameter of the single use endoscope may be equal to or less than 10 mm. In some embodiments, the camera has a diameter of no more than 1 mm. In some embodiments, the illumination element has a diameter of equal or less than 1 mm. In some embodiments, the neck portion has a reduced size as compared to the distal tip. In some embodiments, the camera comprises CMOS or CCD sensor. In some embodiments, the illumination element is selected from light transmission fibers, LEDs, or combination thereof. In some embodiments, the distal tip is a rigid tube with a predefined shape. In some embodiments, the cross section of the distal is selected from circular, oval, square, and rectangle. In some embodiments, the rigid tube is composed of a material selected from metal, flexible, and ceramic. In some embodiments, the distal tip is a shrink tube without a predefined shape. In some embodiments, the shrink tube is selected from a heat shrink tube, cold shrink tube, radiation shrink tube, mechanically activated shrink tube, and electrically activated shrink tube. In some embodiments, the distal tip functions as the illumination element. In some embodiments, the distal tip is composed of a light transmitting material having light conduction capability. In some embodiments, the light transmitting material is selected from PMMA, Poly (methyl methacrylate), Crylux, Plexiglas, Acrylite, Lucite, and Perspex. In some embodiments, the endoscope further comprises one or more working channels. In some embodiments, the working channel is for delivering an instrument. In some embodiments, the working channel is a flexible tube with an adjustable shape. In some embodiments, the working channel is the illumination element composed of a light transmitting material having light conduction capability. In some embodiments, the neck portion and the distal tip are connected through gluing, bonding, or laser welding. In some embodiments, the distal tip shrouds onto the neck portion to join with the neck portion. In some embodiments, the neck portion and the distal tip is an integral single-piece. In some embodiments, the neck portion and the shaft is an integral single-piece. In some embodiments, the distal tip is slidable relative to the neck portion. In some embodiments, endoscope further comprises one or more fluid ports. In some embodiments, the fluid ports reside at the distal tip of the endoscope. In some embodiments, the endoscope comprises an articulation structure. In some embodiments, the articulation structure comprises an array of slot. In some embodiments, the array of slot resides at the distal end of the shaft of the endoscope. In some embodiments, the array of slot resides at the neck portion of the endoscope. In some embodiments, the array of the slot resides at the distal tip of the endoscope. In some embodiments, the array of slot further functions as fluid ports. In some embodiments, the endoscope comprises one or more pull wires for controlling the direction of the articulation structure. In some embodiments, the endoscope comprises two pull wires. In some embodiments, the one or more pull wires are anchored to the distal tip. In some embodiments, the endoscope comprises a user control unit to control the one or more pull wires. In some embodiments, the shaft is a shrink tube without a predefined shape. In some embodiments, the shrink tube is selected from a heat shrink tube, cold shrink tube, radiation shrink tube, mechanically activated shrink tube, and electrically activated shrink tube. In some embodiments, the proximal end comprises one or more compartments. In some embodiments, at least one of the compartments is a fluid chamber. In some embodiments, at least one of the compartments is a dry chamber. In some embodiments, the proximal end comprises an illumination source to transmit light through the light transmitting material.

In another aspect, provided herein is a miniaturized single use endoscope comprising a distal tip, a shaft, a neck portion connecting the distal tip and the shaft, a proximal end, a camera residing at the distal end of the distal tip, wherein the distal tip is composed of a light transmitting material.

In still another aspect, provided is a miniaturized single use endoscope comprising a distal tip, a shaft, a neck portion connecting the distal tip and the shaft, a proximal end, a camera residing at the distal end of the distal tip, and a working channel inside the endoscope, wherein the working channel is composed of a light transmitting material.

In another aspect, provided is an endoscope system comprising the endoscope as described herein and a hand piece. In some embodiments, the hand piece is re-usable. In some embodiments, the hand piece is single-use. In some embodiments, the endoscope and the hand piece are connected via an interface. In some embodiments, the interface provides electrical connection, mechanical connection and illumination alignment. In some embodiments, the hand piece further comprises an illumination source to transmit light through the light transmitting material. In some embodiments, the system further comprises a user control unit for controlling the articulation structure. In some embodiments, the user control unit comprises a turning knob connected to the one or more pull wires to control the direction of the articulation structure. In some embodiments, the user control unit comprises a lever to pull or release the one or more pull wires to control the direction of the articulation structure. In some embodiments, the system further comprises a user interface. In some embodiments, the hand piece is connected to user interface via a cable or wireless. In some embodiments, the wireless is WIFI or Bluetooth. In some embodiments, the system is connected to a computer system. In some embodiments, the system is connected to the computer system via a cable or wireless. In some embodiments, the wireless is WIFI or Bluetooth. In some embodiments, the system further comprises a sterile drape to keep the hand piece sterile during operation. In some embodiments, the sterile drape is a drape bag. In some embodiments, the sterile drape further covers the cable of the hand piece.

In another aspect, provided is a surgical port placement device, comprising a cannula, a hand piece which can connect with the cannula, an obturator inserted into the cannula, a camera and an illumination element residing at the distal end of the port placement device. In some embodiments, the camera and the illumination element reside at the distal end of the cannula. In some embodiments, the camera and the illumination element reside at the distal end of the obturator. In some embodiments, the camera has a diameter of equal or less than 10 mm. In some embodiments, the camera has a diameter of equal or less than 1 mm. In some embodiments, the camera comprises CMOS or CCD sensor. In some embodiments, the camera is connected to the hand piece via a cable. In some embodiments, the illumination element has a diameter of equal or less than 10 mm. In some embodiments, the illumination element has a diameter of equal or less than 1 mm. In some embodiments, the illumination element is selected from light transmission fibers, LEDs, or combination thereof. In some embodiments, the illumination element is one or more LEDs connected to the hand piece via a cable. In some embodiments, the hand piece further comprises an illumination source to transmit light through the light transmission fibers. In some embodiments, the hand piece comprises an electrical unit to supply power to the camera and/or the illumination source. In some embodiments, the hand piece and the cannula are connected via an interface. In some embodiments, the interface is a mechanical interface. In some embodiments, the hand piece comprises one or more buttons for controlling the camera and/or the illumination element. In some embodiments, the cannula system further comprises a user interface connected with the hand piece. In some embodiments, the user interface and the hand piece are connected via a cable or wireless. In some embodiments, the wireless is WIFI or Bluetooth. In some embodiments, the camera and/or the illumination element reside at the distal end of an endoscope inserted into the cannula. In some embodiments, the endoscope is compatible with inner size of the cannula. In some embodiments, the endoscope is compatible with the hand piece. In some embodiments, the system further comprises a sterile drape to keep the hand piece sterile throughout the port placement. In some embodiments, the sterile drape further covers the cable of the hand piece.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

DETAILED DESCRIPTION

Figures 1A, 1B, 1C, 1D:
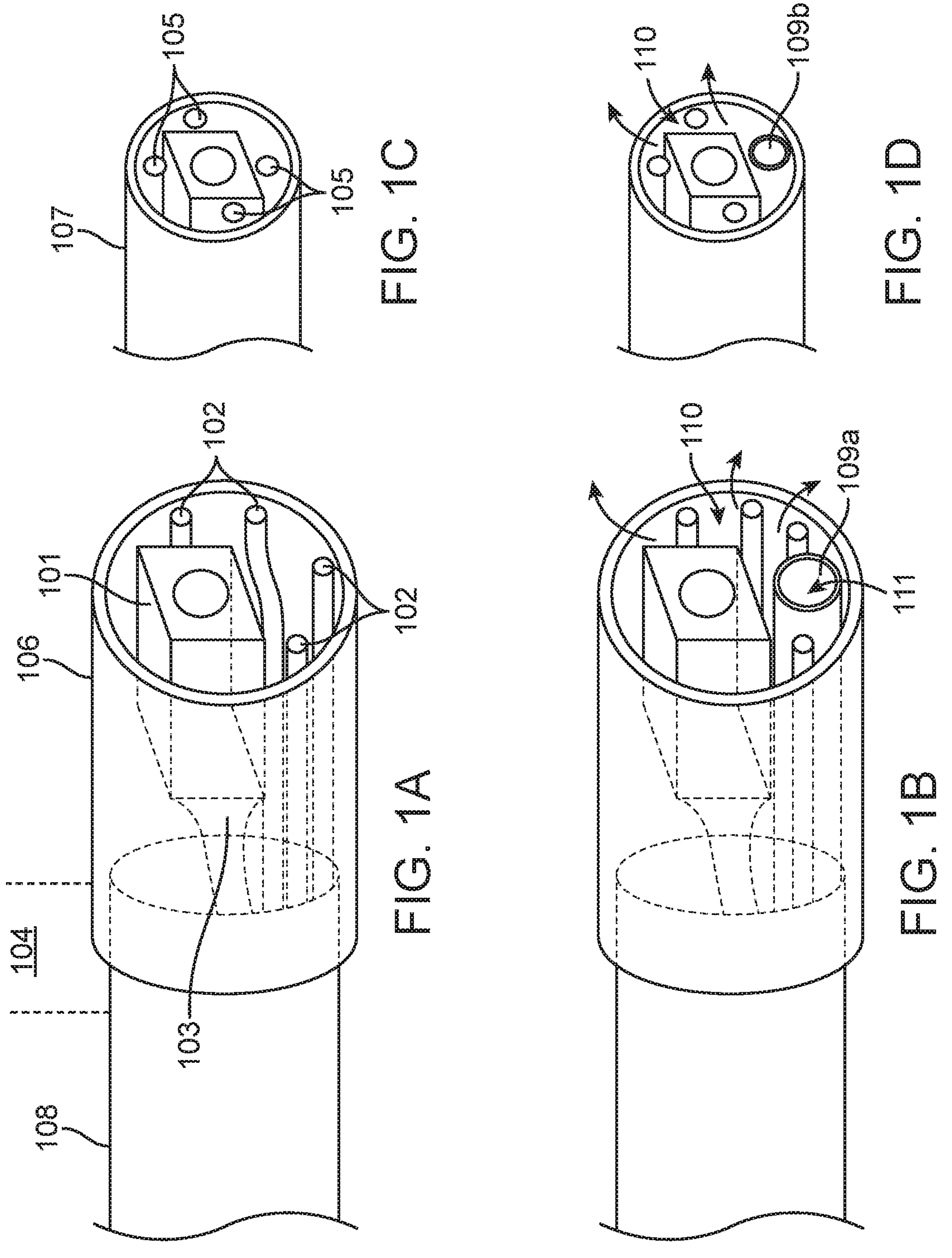
FIG. 1A shows an example of the distal portion of a diagnostic endoscope, in accordance with some embodiments.
FIG. 1B shows an example of the distal portion of an endoscope for therapeutic use, in accordance with some embodiments.
FIG. 1C shows an example of the distal portion of a diagnostic endoscope, in accordance with some embodiments.
FIG. 1D shows an example of the distal portion of an endoscope for therapeutic use, in accordance with some embodiments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of general diagnosis, general surgery and surgery of various types of tissues and organs, for example. It is to be understood that any one or more of the structures and steps as described herein can be combined with any one or more additional structures and steps of the methods and apparatus as described herein, the drawings and supporting text provide descriptions in accordance with embodiments.

Methods and designs of the endoscope of the present disclosure can be applied to various types of endoscopes such as NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, and SialendoScope.

The methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat.

As used in the specification and claims, the singular forms "a," "an," and "the" include plural references unless the context clearly dictates otherwise. For example, the term "a light transmission filer" includes a plurality of light transmission filers.

Whenever the term "at least," "greater than," or "greater than or equal to" precedes the first numerical value in a series of two or more numerical values, the term "at least," "greater than" or "greater than or equal to" applies to each of the numerical values in that series of numerical values.

For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein a processor encompasses one or more processors, for example a single processor, or a plurality of processors of a distributed processing system for example. A control unit or processor as described herein generally comprises a tangible medium to store instructions to implement steps of a process, and the processor may comprise one or more of a central processing unit, programmable array logic, gate array logic, or a field programmable gate array, for example. In some cases, the one or more processors may be a programmable processor (e.g., a central processing unit (CPU) or a microcontrol unit), digital signal processors (DSPs), a field programmable gate array (FPGA) and/or one or more Advanced RISC Machine (ARM) processors. In some cases, the one or more processors may be operatively coupled to a non-transitory computer readable medium. The non-transitory computer readable medium can store logic, code, and/or program instructions executable by the one or more processors unit for performing one or more steps. The non-transitory computer readable medium can include one or more memory units (e.g., removable media or external storage such as an SD card or random access memory (RAM)). One or more methods or operations disclosed herein can be implemented in hardware components or combinations of hardware and software such as, for example, ASICs, special purpose computers, or general purpose computers.

The term "endoscope" as used herein refers to a tubular instrument (a type of borescope) used to look deep into the body and used in procedures called an endoscopy. It can be used to examine the internal organs, such as throat or esophagus. In some embodiments, the endoscope of the present disclosure includes specialized endoscopes named after their target organs. They can be used to examine and diagnose the affected site, or to assist in surgeries such as laparoscopy. The specialized endoscope of the present disclosure includes but is not limited to NeuroendoScope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, and ColonoScope.

The terms "distal" and "proximal" as used herein refer to locations referenced from the apparatus and can be opposite of anatomical references. For example, a distal location of a endoscope may correspond to a proximal location of the patient, and a proximal location of the endoscope may correspond to a distal location of the patient.

Miniaturized Single Use Endoscope

For conventional endoscopes, the imaging device such as camera may reside at the proximal end or in the hand piece held by a physician so that at least the camera can be reused to reduce cost. Furthermore, conventional endoscopes can be large in size, with diameters at centimeter scale. Endoscope with reduced dimension is desired to allow for less invasive procedure with a smaller incision access to the body, which can lead to better outcome of the patient. However, reducing the dimension or size of endoscopes can be difficult without sacrificing the desired performance or functionality of the endoscopes due to the increased cost in manufacture, assembly, and lacking of compact design.

In one aspect, provided herein is a miniaturized single use endoscope. The provided single-use endoscope can be entirely disposable. This may beneficially reduce the requirement of sterilization which can be high in cost or difficult to operate, yet the sterilization or sanitization may not be effective. The provided endoscope may have a compact design or configuration such that overall size of the endoscope may be reduced. In some embodiments, the provided endoscope may be miniaturized single-use endoscope with an overall size such as the diameter of no more than 2-3 mm.

In some embodiments, the miniaturized, single-use endoscope may comprise a distal tip, a shaft, a neck portion connecting the distal tip and the shaft. The miniaturized, single-use endoscope may also comprise a proximal end, and one or more electronic elements such as camera and illumination element residing at the distal tip.

In some embodiments, the miniaturized, single-use endoscope may comprise one or more electronic components located at the distal tip. The one or more electronic components may comprise an imaging device, illumination element or sensors.

In some embodiments, the imaging device may be a video camera. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

In some embodiments, the camera may be a tiny camera that may have a dimension range from a few millimeters to sub-millimeter. The camera may have a dimension (e.g., length, width) of equal or less than 1 mm. In some embodiment, the camera has a diameter of equal or less than 0.9 mm, 0.8 mm, 0.7 mm, 0.6 mm, 0.5 mm, 0.4 mm, 0.3 mm, 0.2 mm, or 0.1 mm.

In some embodiments, the illumination element may comprise one or more light sources positioned at the distal tip. The light source may be a light-emitting diode (LED), an organic LED (OLED), a quantum dot, or any other suitable light source. In some cases, the light source may be miniaturized LED for a compact design or Dual Tone Flash LED Lighting. The illumination element can include any suitable illumination means, which emit light for illuminating the target site. The illumination element includes but is not limited to light transmission fibers, LEDs, and the combination thereof. In some embodiments, there is one LED residing at the distal end of the endoscope as the illumination element. In some embodiments, there are more two or more LEDs residing at the distal end of the endoscope as the illumination element. In some embodiments, there are one or more light transmission fibers at the distal end of the endoscope as the illumination elements. In some embodiments, there are a bundle of light transmission fibers at the distal end of the endoscope as the illumination elements. In some embodiments, an illumination source such as a LED source is placed at the proximal end of the endoscope or the hand piece, and the illumination source can transmit light through the light transmission fibers to the distal end of the endoscope. In some embodiments, there are both LEDs and light transmission fibers at the distal end of the endoscope as the illumination elements.

In some embodiments, the illumination element residing at the distal end of the endoscope may have a dimension (e.g., length, width) of equal to or less than 1 mm. In some embodiment, the illumination element may have a diameter of equal or less than 0.9 mm, 0.8 mm, 0.7 mm, 0.6 mm, 0.5 mm, 0.4 mm, 0.3 mm, 0.2 mm, or 0.1 mm.

In some embodiments, an additional or separate illumination light source (e.g., LED light source) may be located at the distal end of the endoscope. In some embodiments, the endoscope may comprise an illumination structure integral to the distal tip without requiring an additional illumination light source present at the distal tip. In some cases, the illumination element may be integral to the distal tip. In some cases, the enclosure of the distal tip may be designed to provide illumination light. For instance, the enclosure of the distal tip may be composed of a light transmitting material with light conduction capability, which can function as the illumination element. The enclosure structure of the distal tip may emit light transmitted from the illumination source located at the proximal end or hand piece. This may beneficially reduce a separate or extra light source located at the distal tip thereby advantageously reducing the size of the distal tip. The enclosure of the distal tip can be made of any suitable materials with light conduction capability such as PMMA, Poly (methyl methacrylate), Crylux, Plexiglas, Acrylite, Lucite, and Perspex.

In some embodiments, a working channel placed inside the endoscope may be composed of a light transmitting material with light conduction capability, and the working channel may function as the illumination element at the distal end, which emits light transmitted from the illumination source placed at the proximal end or hand piece.

In some embodiments, the distal tip of the provided endoscope may comprise an enclosure such as a rigid tube with a predefined rigid shape. In some embodiments, the rigid tube may be composed of rigid materials such as metal, ceramic or polymers as long as desired rigidity can be provided. The predefined shape (e.g., cross-section) of the rigid tube may include but is not limited to circular, oval, square, and rectangle. Alternatively, the distal tip of the provided endoscope may comprise an enclosure such formed from a shrink tube without a predefined shape. Shrink tube may be tubes composed of flexible and shrinkable materials. These shrink tubes may provide protective environment for the elements residing inside the endoscope and have desired flexibility and may shrink to wrap around the inside elements. In some embodiments, the distal tip may comprise a shrink tube without a predefined shape. Examples of shrink tubes of the present disclosure include but are not limited to heat shrink tubes, cold shrink tubes, radiation shrink tubes, mechanically activated shrink tubes, electrically activated shrink tubes and the like.

In some embodiments, the distal tip and the neck portion of the endoscope may be an integral single-piece element. In some embodiments, the distal tip and the neck portion of the endoscope may be separate and individual pieces which may be coupled together. The distal tip and the neck portion can be connected through a suitable connection method such as gluing, bonding, mechanical connection or laser welding.

In some embodiments, the neck portion may have a diameter smaller than that of the distal tip of the endoscope such that the neck portion may at least partially surround the distal tip. In some embodiments, the neck portion may a diameter smaller than that of the distal tip of the endoscope such that the neck portion may be at least partially surround by the distal tip. In some embodiments, the distal tip shrouds onto at least part of the neck portion so that to join with the neck portion. In some embodiments, the neck portion shrouds onto the distal tip so that to join with the distal tip. In some embodiments, the distal tip may be slidable relative to the neck portion. In some embodiments, the neck portion and the shaft may be an integral single-piece element.

The shaft of the provided endoscope may be an elongate member. In some embodiments, the shaft may comprise a rigid tube with a predefined shape. Alternatively, the shaft may comprise a shrink tube without a predefined shape. In some embodiments, the rigid tube may be composed of suitable materials for desired flexibility or bending stiffness. In some cases, the materials of the shaft may be selected such that it may maintain structural support to the internal structures (e.g., working channel) as well as being substantially flexible (e.g., able to bend in various directions and orientations). For example, the shaft can be made of any suitable material such as Provista Copolymer, vinyl (such as polyvinyl chloride), Nylon (such as vestamid, grillamid), pellethane, polyethylene, polypropylene, polycarbonate, polyester, silicon elastomer, acetate and so forth. In some cases, the materials may be polymer material, bio-compatible polymer material and the shaft may be sufficiently flexible to be advancing through a path with a small curvature without causing pain to a subject. The predefined shape (cross-section) of the rigid tube may include but is not limited to circular, oval, square, and rectangle. In some embodiments, the shaft may comprise a shrink tube without a predefined shape. Such shrink tube may include but is not limited to heat shrink tube, cold shrink tube, radiation shrink tube, mechanically activated shrink tube, and electrically activated shrink tube.

In some embodiments, the endoscope of the present disclosure may further comprise a working channel for delivering instrument. Various surgical instruments can be delivered through the working channel. Exemplary instruments include but are not limited to biopsy tools, brushes or forceps. In some embodiments, the endoscope may comprise one working channel. In some embodiments, the endoscope of the present disclosure may comprise multiple working channels, such as two, three, four, five or more working channels. In some embodiments, the working channel may comprise a rigid tube composed of any desirable materials. The materials can be the same as those materials as described above. In some embodiments, the working channel may comprise a shrink tube without a predefined shape, such as heat shrink tube, cold shrink tube, radiation shrink tube, mechanically activated shrink tube, or electrically activated shrink tube.

In some embodiments, the endoscope may further comprise one or more fluid ports for fluid communication such as fluid inflow or outflow. In some embodiments, the fluid ports may locate at the distal end of the endoscope. In some embodiments, the fluid ports may locate at the neck portion of the endoscope. In some embodiments, the fluid ports may locate at the shaft of the endoscope. In some embodiments, the endoscope may comprise one or more arrays of fluid ports on the outer surface of the endoscope.

In some embodiments, the provided endoscope may comprise an articulation structure allowing for a compact configuration of the endoscope. The articulation structure may be structures integrally formed with the neck portion to provide articulation of the endoscope. In some embodiments, a distal end of one or more pull wires may be anchored or integrated to the distal tip, such that operation of the pull wires by the control unit may apply force or tension to the distal tip which may steer or articulate (e.g., up, down, pitch, yaw, or any direction in-between) at least the articulation structure (e.g., neck portion) of the endoscope.

In some embodiments, the articulation structure may be capable or achieving a desired bending degree. In some embodiments, the bending degree can be at least 5, at least 10, at least 15, at least 30, at least 60, at least 70, at least 90, or more degrees in up, down, pitch, yaw, or any direction in-between.

In some embodiments, the articulation structure may comprise an array of cuts/slots structure formed at the neck portion such that the neck portion can be articulated. Traditional articulating structures often require use of additional elements such as pivots, hinges, and the like to achieve articulation. By introducing the cuts or slots structure in the shaft or the neck portion of the endoscope directly, articulation can be achieved without extra components which beneficially reduce the dimensional, size, footprint, weight, or materials of the endoscope.

In some embodiments, the array of cuts/slots may reside next to the distal end of the shaft. In some embodiments, the array of cuts/slots may reside at the neck portion. In some embodiments, the array of cuts/slots may reside next to the neck portion. In some embodiments, the articulation structure may comprise one or more arrays of cuts/slots. In some embodiments, each array of the slots can comprise at least two, three, four, five, six, seven, eight, nine, ten, or more cuts/slots. In some embodiments, each slot in the array can have the same size. In some embodiments, the cuts/slots in the array can have the different sizes.

In some embodiments, the slots may function as the fluid ports of the endoscope. The fluid ports may be provided for fluid communication, such as inflow or outflow of fluid. Fluids that can be used in the present disclosure include but are not limited to water, saline, therapeutic agents and anesthetics. A vapor or gaseous can also be transferred through the ports, such as, for example, air, carbon dioxide, nitrogen and the like.

In some embodiments, the movement of the articulation structure is controlled by one or more pull wires. The pull wire can be a metallic wire, cable or thread, or it may be a polymeric wire, cable or thread. In some embodiments, the proximal portion of the one or more pull wires can be operatively coupled to various mechanisms (e.g., gears, pulleys, etc.) in the proximal end or hand piece. In some embodiments, the distal portion of the one or more pull wires can be attached to the distal tip of the endoscope, or the distal end of the shaft. In some embodiments, the pull wires may be connected to the inner wall of the endoscope. In some embodiments, the pull wires may be attached to the inner wall of the endoscope. In some embodiments, the one or more pull wires are operatively controlled by a user control unit at the proximal end or hand piece. In some embodiments, the user control unit comprises a turning knob connected to the one or more pull wires to control the direction of the articulation structure. In some embodiments, said user control unit comprises a lever to pull or release the one or more pull wires to control the direction of the articulation structure.

Figure 13:
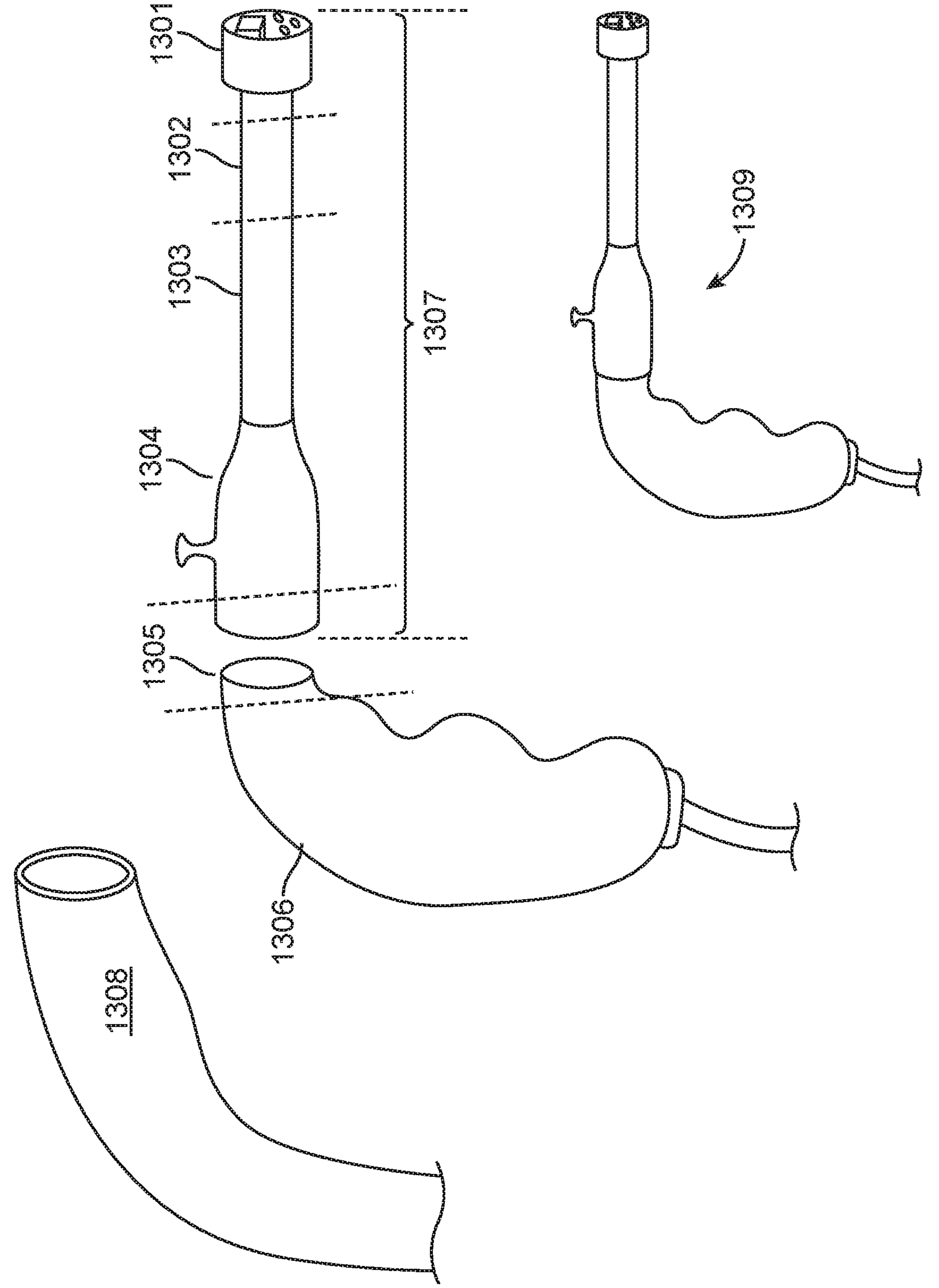
FIG. 13 illustrates an example of a miniaturized single use endoscope, in accordance with some embodiments.

FIG. 13 shows an example of a miniaturized single-use endoscope system of the present application. In some embodiments, the endoscope system may comprise an endoscope 1307 and a hand piece 1306. The endoscope 1307 may comprise a distal tip 1301, a distal articulation structure 1302, a shaft 1303, a proximal end 1304, and an interface 1305 between the endoscope and the hand piece. The distal articulation structure can be the same as the articulation structure as described above.

In some embodiments, the hand piece 1306 may be re-usable. In some embodiments, the endoscope 1307 and hand piece 1306 may be removably attached such that the endoscope may be released from the hand piece and disposed after single-use while the hand piece can be reused. In some cases, the hand piece may comprise a mechanical interface that may allow the endoscope to be releasably coupled to the hand piece. For instance, the handle piece can be attached to the endoscope via quick install/release mechanism, such as magnets and spring-loaded levels. In some cases, the endoscope may be coupled or released from the hand piece manually without using a tool. In some embodiments, a single-use drape 1308 may be used to cover the re-usable hand piece to provide sterility during the procedure.

In alternatively embodiments, the hand piece may be single-use. The hand piece 1309 may be integral to the endoscope as a single element and the entire endoscope including the hand piece may be single-use and disposable.

Compact Miniaturized Distal Tip of the Endoscope

FIG. 1A-FIG. 1D show examples of the distal tips of the endoscopes of the present disclosure. In the example of FIG. 1A, the distal tip may comprise an imaging device such as a camera 101, and illumination element such as light transmission fibers 102. The camera may have any display resolution such as full HD, HD, video graphics array (VGA), or less than VGA. The camera may reside at the distal end, and an electrical cable 103 may be connected to the camera to provide power and for data transmission. The electricity cable and the light transmission fibers may go through neck portion 104 located between the distal tip 106 and shaft 108. The neck portion may have a diameter smaller than the dimeter of the distal tip 106.

FIG. 1B shows an example of an endoscope comprising a working channel 109*a*. The working channel can be used for inserting an instrument. One or more working channels can be fitted into the hollow space 111 of the endoscope.

FIG. 1C shows an example of the distal tip housing LEDs 105 as illumination element. The LEDs may be soldered to electrical wires. The LEDs may have a dimension of equal or less than 1 mm.

In some embodiments, the enclosure of the distal tip 106 is a rigid tube with a predefined shape, such as circular, oval, square, rectangle, and the like. These rigid tubes can be composed of any suitable material such as metal, ceramic, composite material and the like to provide structural support.

In some embodiments, the enclosure 107 of the distal tip may be composed of a flexible material that may not provide substantially structural support to the elements housed by the enclosure. In some cases, the enclosure may not maintain a pre-defined shape. The enclosure may comprise a shrink tube, such as heat shrink tubes, cold shrink tubes, radiation shrink tubes, mechanically activated shrink tubes, electrically activated shrink tubes and the like. In this case, the tube may not maintain a regular circular shape, and can wrap around the elements inside the endoscope. This flexible material allows to minimize the outer perimeters of the endoscope. For example, the heat shrink tube can change to a smaller size under heat condition and therefore tightly shroud around the elements such as working channel in the distal tip. The same shrink tube can also be used in the shaft of the endoscope to generate a smaller outer diameter. In some embodiments, the shaft has a regular pre-defined shape, as shown in 108. In some embodiments, the shaft is composed of a flexible material without a pre-defined shape, such as heat shrink tubes, cold shrink tubes, radiation shrink tubes, mechanically activated shrink tubes, electrically activated shrink tubes and the like, as shown in FIG. 1D.

The example of the endoscope in FIG. 1C can also include a working channel. The working channel can be the same as the working channel as described in FIG. 1B. In some cases, flexible tubes can be used as the working channel to form a more compact structure. As illustrated in FIG. 1D, flexible tube 109*b* with an adjustable shape can be used to allow the shrink tube shrouding more effectively. The flexible tube can change its overall shape from circular to oval or others so that to accommodate the change of the outer shrink tubes. In some embodiments, the shrink tubes may squeeze towards the tube of the flexible tube, and collapse around the working channel.

In some embodiments, fluid may flow through the endoscope. In some embodiments, said fluid may flow in/out through the gaps between elements within the endoscope (camera, light transmission fiber, LEDs and the like). Alternatively, said fluid may flow in/out through the working channel 111. In some embodiments, fluid may flow in/out from the front surface of the distal tip 110. In some embodiments, continuous flow (irrigation and aspiration) can come from the front surface of the distal tip (inflow) and the working channel (outflow as indicated by the outward arrows) or vice versa.

Figure 5:
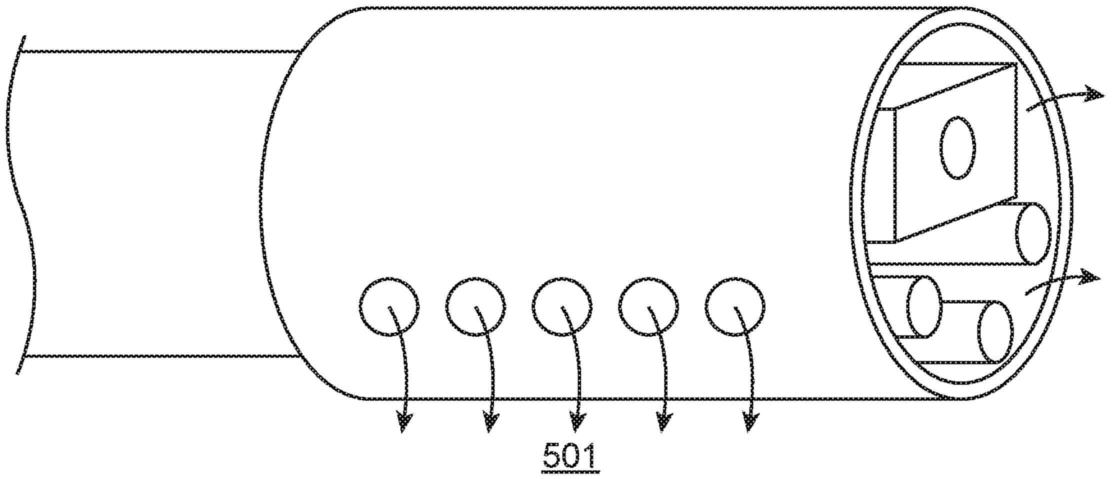
FIG. 5 illustrates an example of a distal portion of an endoscope with fluid ports, in accordance with some embodiments.

In some embodiments, to enhance the fluid flow (inflow or outflow), additional fluid ports 501 can be added at distal tip, as shown in FIG. 5. In some embodiments, the front surface of the distal tip may or may not serve for fluid flow (indicated by the arrows).

Figure 2A:
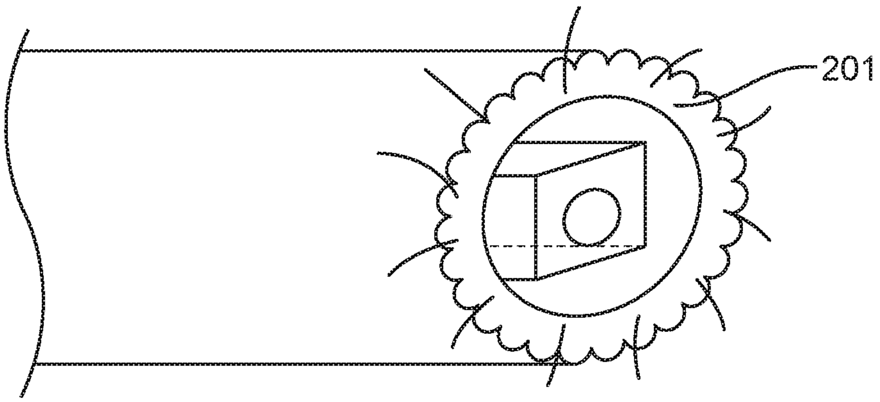
FIG. 2A shows an example of a miniaturized endoscope with illumination walls, in accordance with some embodiments.

FIG. 2A shows an example of a miniaturized endoscope with illumination distal tip. In the example of FIG. 2A, the distal tip may comprise a miniaturized camera and an enclosure 201, and the enclosure 201 may be made of a light transmitting material which has light conduction capabilities. In some embodiments, the cross-section of the illuminating distal tip may be circular, oval, rectangle, or any other suitable shape. This integrated configuration may further reduce a separate or extra light source located at the distal tip thereby advantageously reducing the size of the distal tip.

Figure 2B:
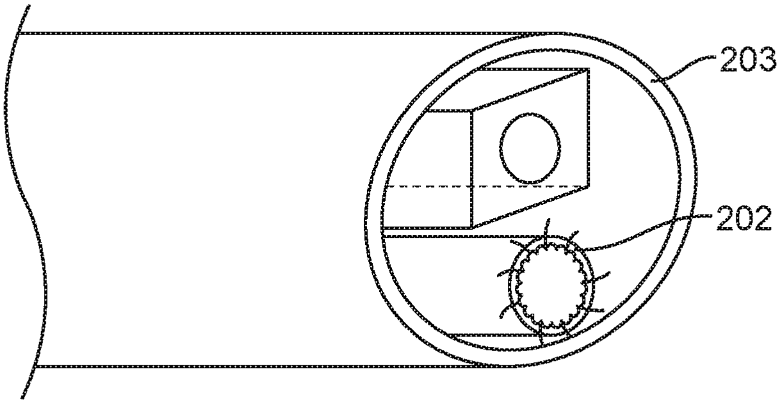
FIG. 2B shows an example of a miniaturized endoscope with illumination working channels, in accordance with some embodiments.

FIG. 2B shows an example of a miniaturized endoscope with illumination working channels. In the example of FIG. 2B, the distal tip may comprise an enclosure 203, a camera, and a working channel 202, and the working channel 203 may be made of a light transmitting material which has light conduction capabilities. In some embodiments, the enclosure 203 may be composed of regular non-light transmission material. Alternatively, the distal dip 203 may be made of a light transmission material to transmit light as well. This integrated configuration may also reduce a separate or extra light source located at the distal tip thereby advantageously reducing the size of the distal tip.

Figure 2C:
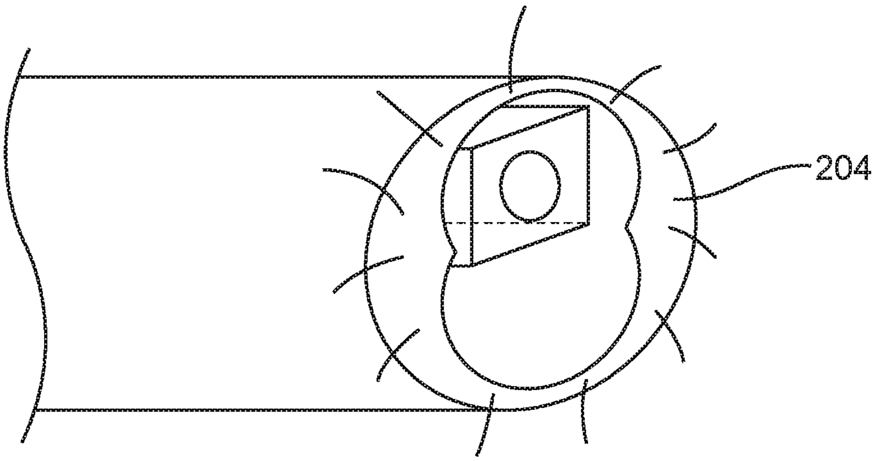
FIG. 2C shows an example of a miniaturized endoscope with multi-lumen illumination walls, in accordance with some embodiments.

FIG. 2C shows an example of a miniaturized endoscope with a multi-lumen illumination structure. In the example of FIG. 2C, the distal tip 204 may have a multi-lumen structure. The distal tip may be composed of a light transmitting material which has light conduction capabilities. In some embodiments, compartments can be designed within the multi-lumen structures for placing the camera, one or more working channels, and the like. This integrated configuration may reduce a separate or extra light source located at the distal tip thereby advantageously reducing the size of the distal tip.

Articulation Structure of the Endoscope

Figure 3A:
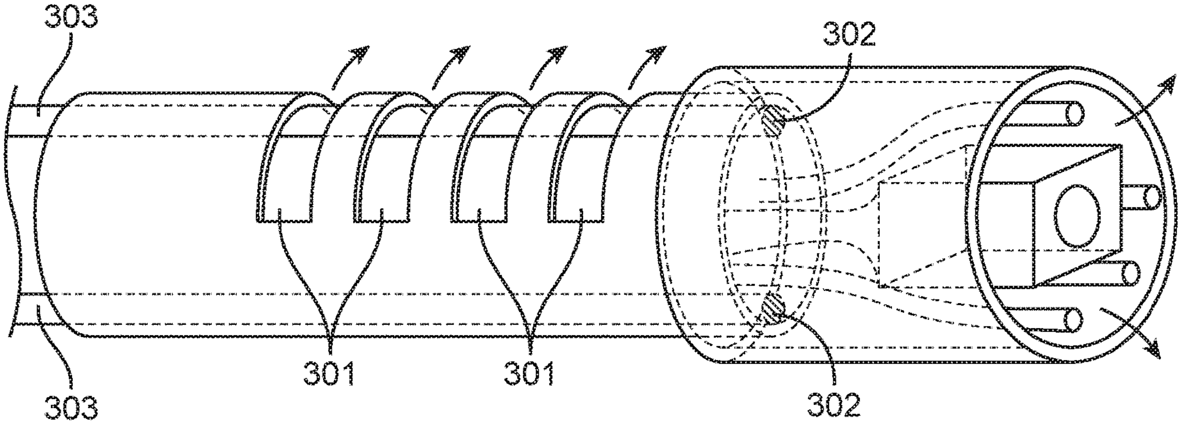
FIG. 3A illustrates an example of an articulation structure, in accordance with some embodiments.

In some embodiments, the miniaturized endoscope of the present disclosure may comprise an articulation structure. FIG. 3A illustrates an example of the articulation structure. In the example of FIG. 3A, the articulation structure is an array of slots 301 formed at the distal end of the shaft. The articulation (bending) occurs at the array of slots. The matriculation may be controlled by the pull wires 303. In some embodiments, the pull wires 303 can be attached to the inner wall of the endoscope, and the distal portion of the pull wire 302 is anchored to the distal end of the shaft. In some embodiments, the pull wires may be operatively controlled by a user control unit at the proximal end or hand piece.

Figure 3B:
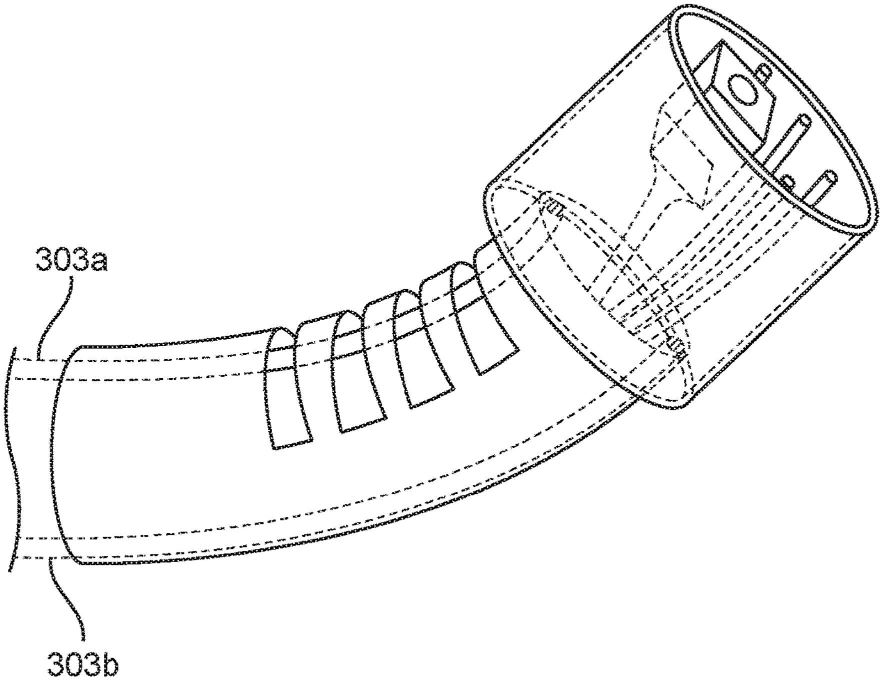
FIG. 3B illustrates an example of an endoscope with integral articulation structure, in accordance with some embodiments.

FIG. 3B illustrates an example of an endoscope with integral articulation structure. In the example of FIG. 3B, the articulation structure is an array of slots that can be articulated into multiple directions upon pulling by two pull wires. When the pull wire 303*a* is pulled, depending on the force applied, the slots may close up and the distal tip of the endoscope may bend up for a certain degree. When the pull wire 303*a* is released, the distal tip may spring back to the original state as shown in FIG. 3A. Similarly, when the pull wire 303*b* is pulled, the slots may close up and the distal tip may bend down for a certain degree. Releasing 303*b* allows the distal tip resuming back to the natural state. In some embodiments, the slots can also function as the fluid ports for fluid inflow or outflow (indicated by outward arrows), similar as the fluid ports 501 in FIG. 5.

Figure 4A:
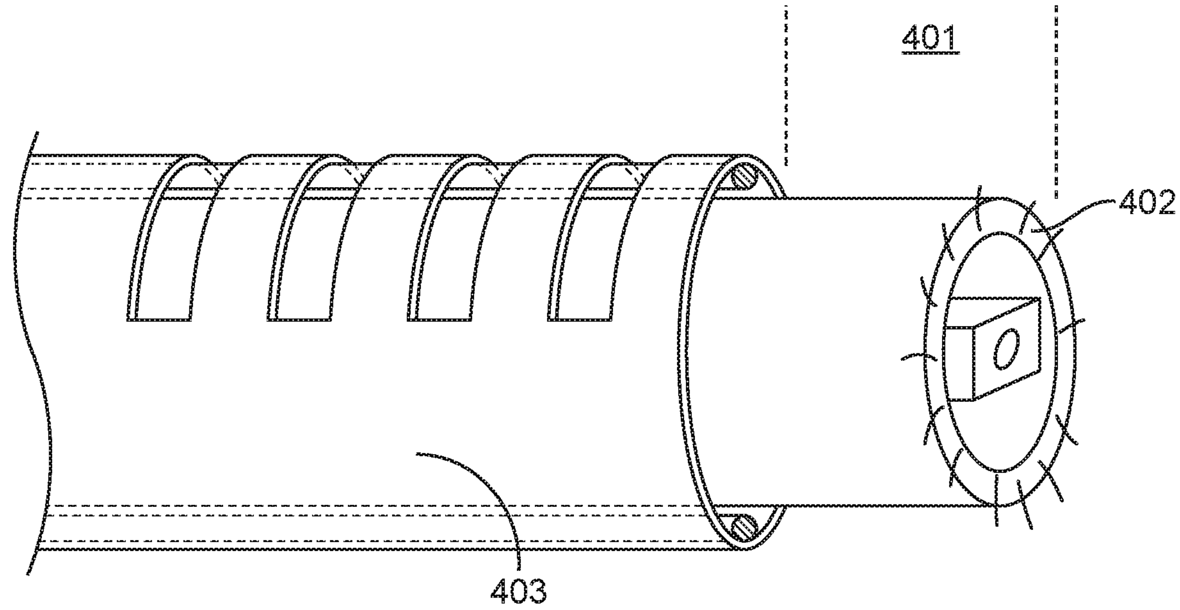
FIG. 4A illustrates an example of a configuration of a miniaturized endoscope with an articulation structure, in accordance with some embodiments.
Figure 4B:
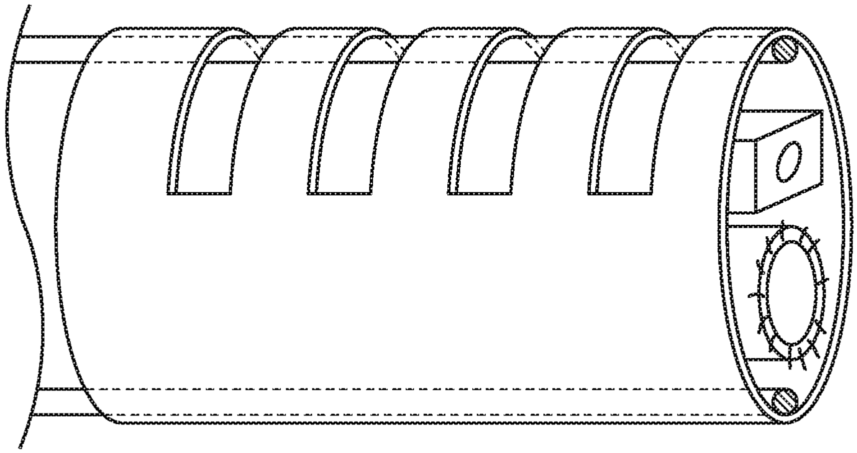
FIG. 4B illustrates an example of another configuration of a miniaturized endoscope with an articulation structure, in accordance with some embodiments.

FIGS. 4A and 4B illustrate example configurations of a miniaturized endoscopes with an articulation structure. FIG. 4A shows an example of adjustable articulation structure. In the example of FIG. 4A, the distal tip may comprise an inner tube 402 which can slide in or out relative to the outer articulation shaft 403. The exposed portion 401 of the inner tube may be extended over the outer articulation shaft 403 such that the location of articulation relative to the tip end of the distal tip can be controlled. For instance, by controlling the length of the exposed portion 401 (e.g., sliding the inner tube 402 relative to the outer articulation shaft 403), a desired location for the articulation relative to the distal end of the distal tip can be adjusted during the use of the device. In some embodiments, the inner tube 402 can be composed of a light transmitting material having light conduction capability.

FIG. 4B shows another example of the configuration of the miniaturized endoscope with an articulation structure. In the example of FIG. 4B, the articulation shaft is the enclosure of the distal tip, which encloses the working channel, and the camera. The camera may reside inside the articulation shaft at the distal end. This may beneficially provide a compact design allowing for a reduced size of the endoscope. In some embodiments, the working channel can be composed of light transmitting material having light conduction capability. These integrated configurations may significantly reduce the overall size of the endoscope meanwhile achieve the same functions as the conventional articulating endoscopes.

Shaft Design of the Endoscope

The shafts of conventional endoscopes are typically composed of rigid or semi-rigid materials, such as metal, ceramic and the like. As described above, the shaft herein may comprise a rigid tube with a predefined shape. Alternatively, the shaft may comprise a shrink tube without a predefined shape. In some embodiments, the rigid tube may be composed of suitable materials for desired flexibility or bending stiffness. In some cases, the materials of the shaft may be selected such that it may maintain structural support to the internal structures (e.g., working channel) as well as being substantially flexible (e.g., able to bend in various directions and orientations). For example, the shaft can be made of any suitable material such as Provista Copolymer, vinyl (such as polyvinyl chloride), Nylon (such as vestamid, grillamid), pellethane, polyethylene, polypropylene, polycarbonate, polyester, silicon elastomer, acetate and so forth. In some cases, the materials may be polymer material, bio-compatible polymer material and the shaft may be sufficiently flexible to be advancing through a path with a small curvature without causing pain to a subject. The predefined shape (cross-section) of the rigid tube may include but is not limited to circular, oval, square, and rectangle. In some embodiments, the shaft may comprise a shrink tube without a predefined shape. Such shrink tube may include but is not limited to heat shrink tube, cold shrink tube, radiation shrink tube, mechanically activated shrink tube, and electrically activated shrink tube. By using the shrink tube, the shaft may shroud and squeeze to contact with the internal structure (such as the light transmission fibers, electrical wires, working channels and the like) so that to reduce the dimension (outer perimeters) of the shaft.

In some embodiments, the distal tip and the shaft of the endoscope may both be composed of shrink tubes without a pre-defined shape, such as heat shrink tubes, cold shrink tubes, radiation shrink tubes, mechanically activated shrink tubes, electrically activated shrink tubes and the like. This design can minimize the dimension (outer perimeters) of the endoscopes.

Illumination Element of the Endoscope

Conventional endoscopes use a light fiber bundle to illuminate, which requires a light source. The light source is normally an external light box, for example, Xenon, Laser and the like. These light sources are very expensive and are standalone from the endoscope.

Figure 6:
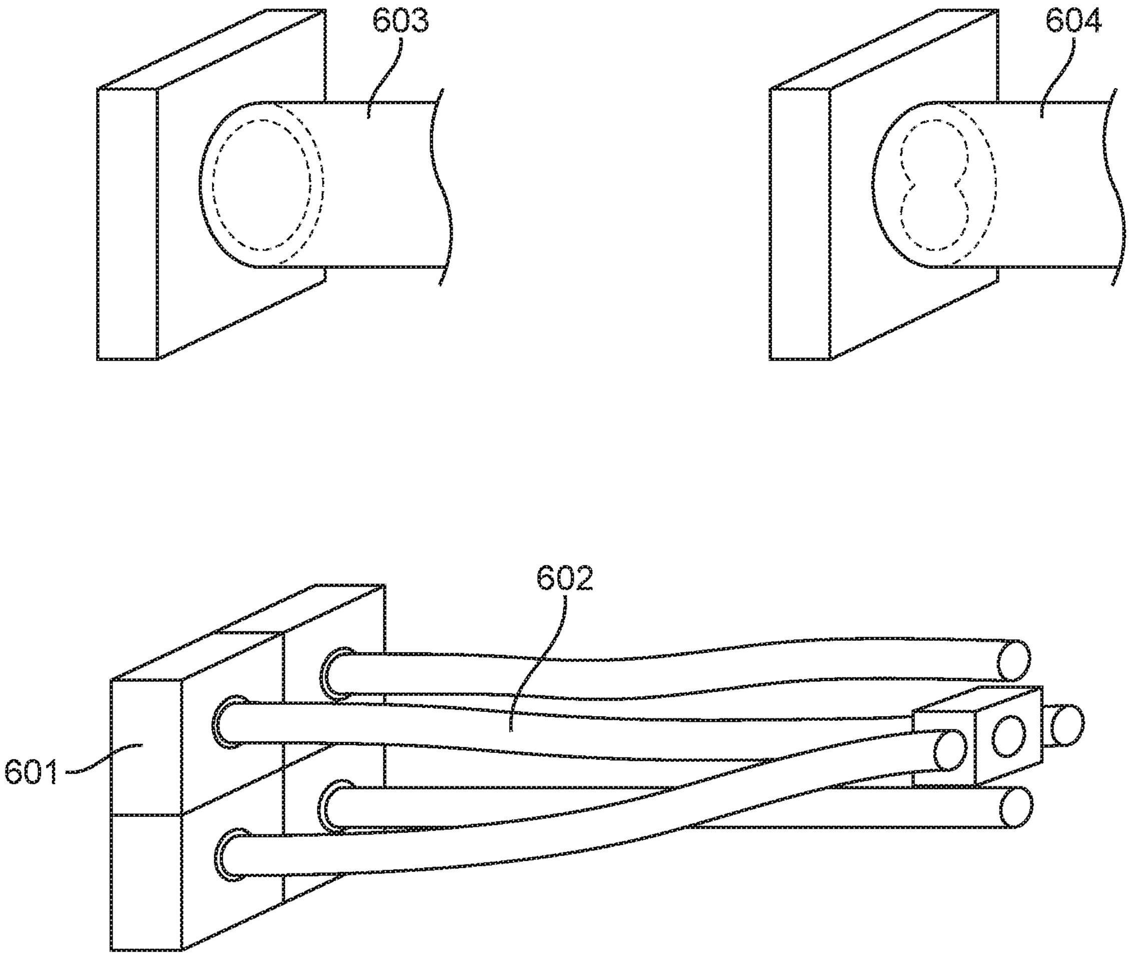
FIG. 6 illustrates an example of illumination sources at the proximal end of an endoscope, in accordance with some embodiments.

In some embodiments, the illumination element may be a LED directly placed at the distal end of the endoscope. In some embodiments, an illumination source such as a LED source is placed at the proximal end of the endoscope or the hand piece, and the illumination source can transmit light through the light transmission fibers or other light transmission structures to the distal end of the endoscope. FIG. 6 shows some examples of illumination sources at the proximal end of an endoscope. In these examples, one or more LEDs 601 may be located at the proximal end. Light transmission fibers 602, illumination tube 603 or customized illumination configuration 604 may align with the LEDs 601 at the proximal end, which allow light from LED transmitting through the illumination fibers 602, tubes 603 or customized illumination configuration 604. In some embodiments, the LEDs 601 can be placed at the proximal end of the endoscope 1304. In some embodiments, the LEDs 601 can be placed in the hand piece 1306, as shown in FIG. 13.

Proximal End of the Endoscope

Figure 7:
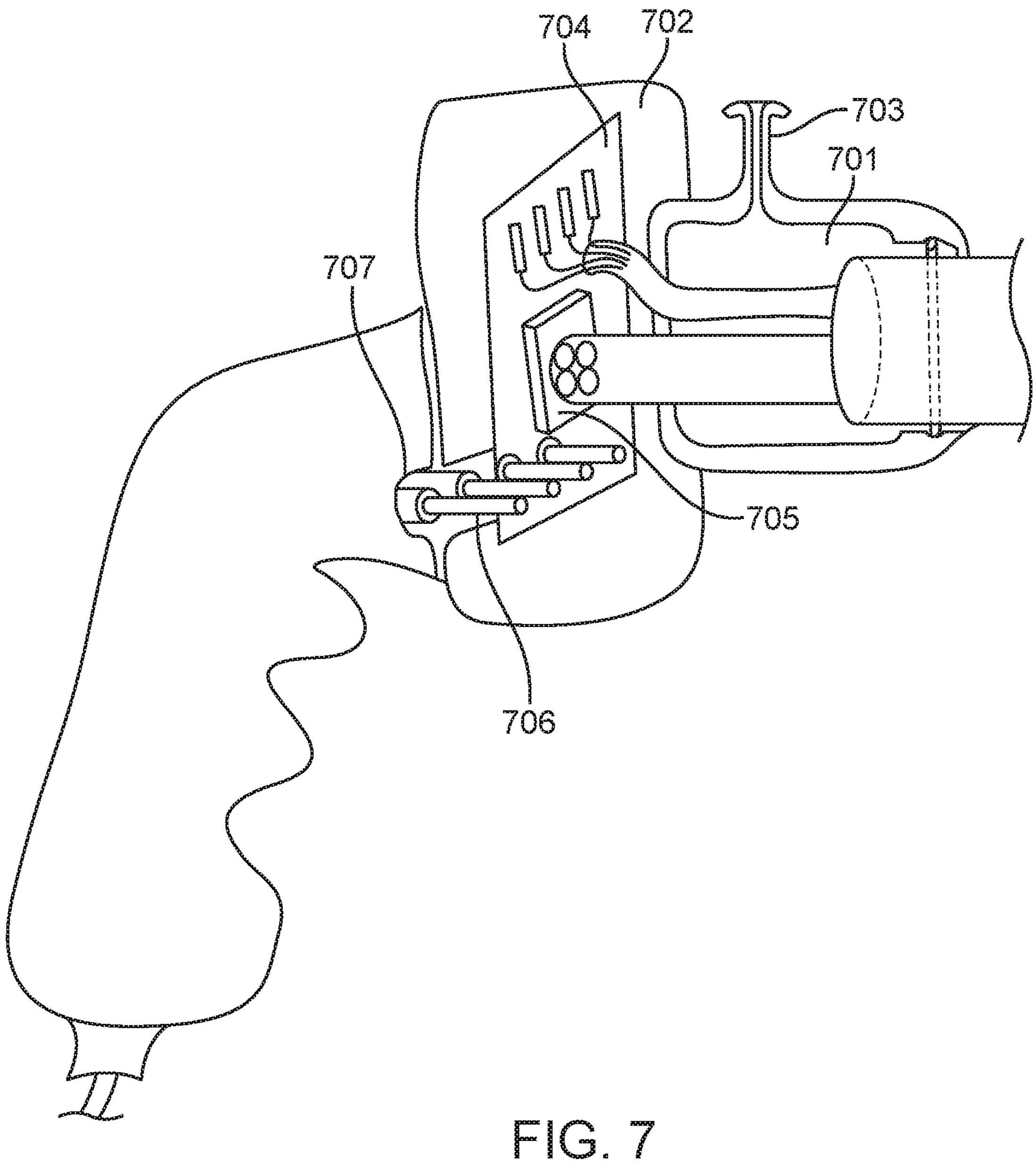
FIG. 7 illustrates an example of a proximal end of the endoscope having an illumination source coupled with a hand piece, in accordance with some embodiments.
Figure 8:
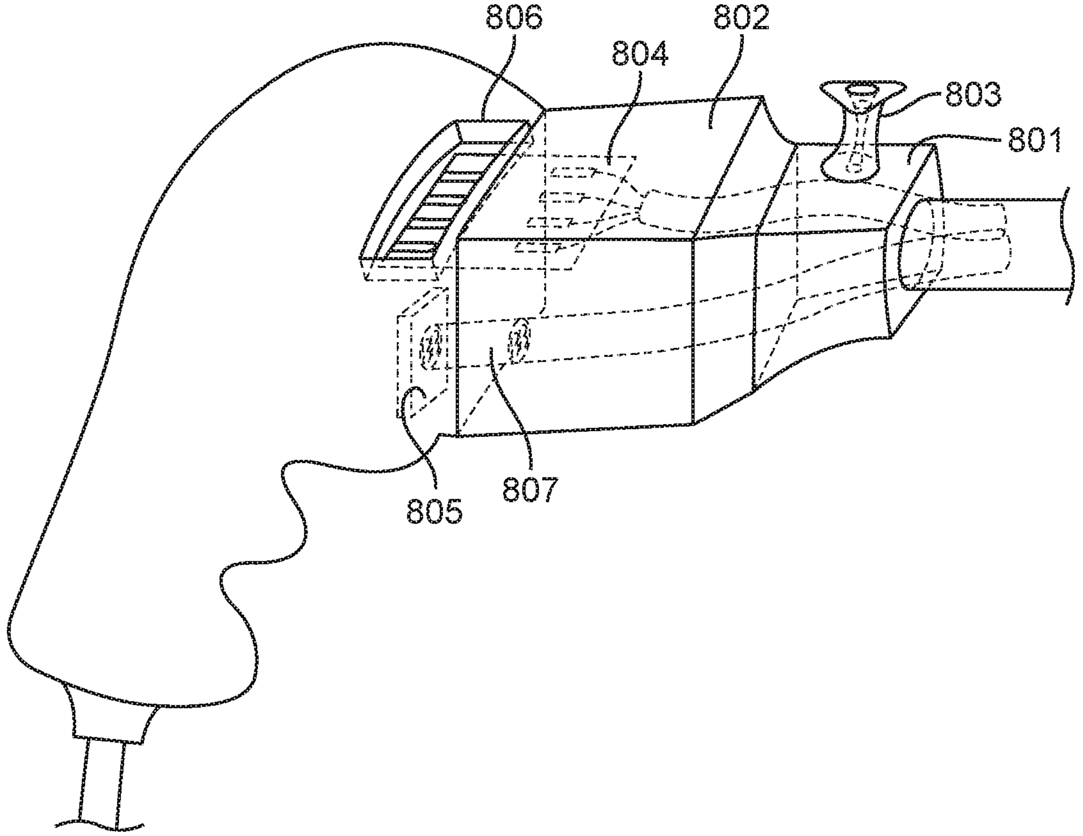
FIG. 8 illustrates an example of a proximal end of the endoscope coupled with a hand piece having an illumination source, in accordance with some embodiments.
Figure 9:
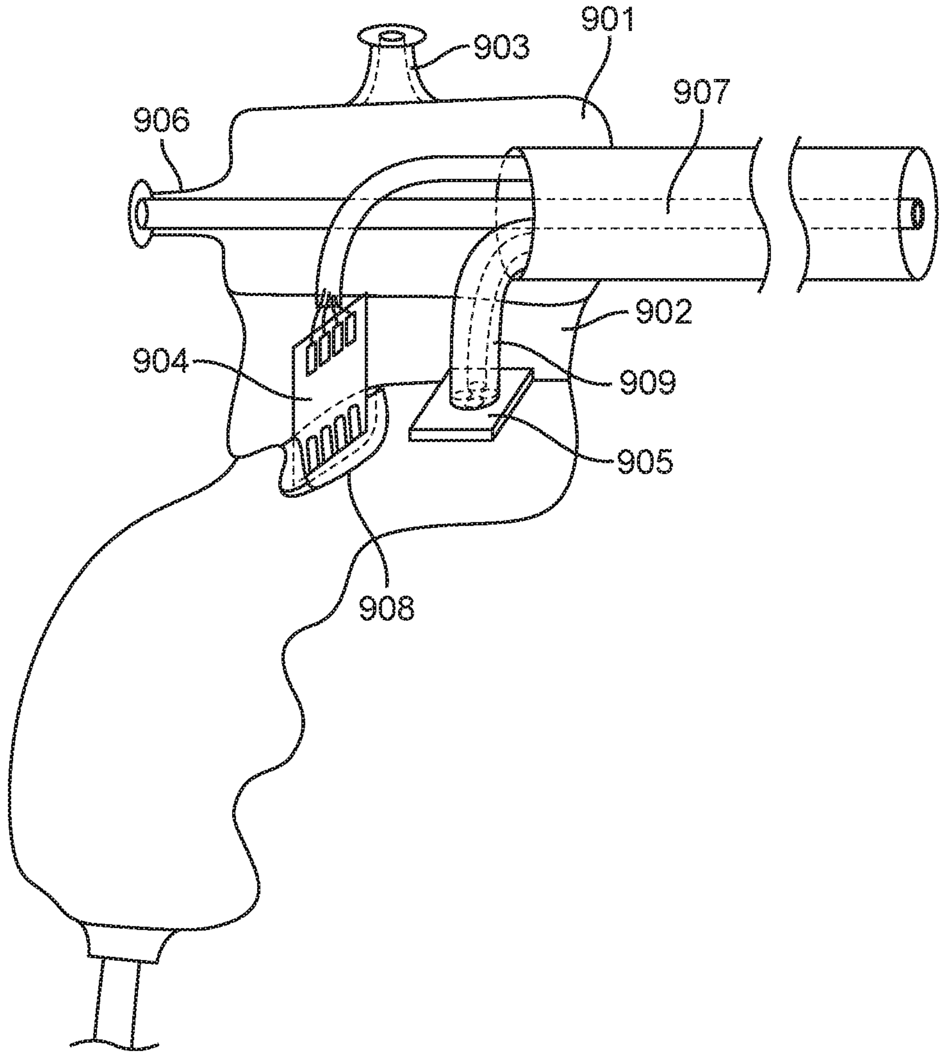
FIG. 9 illustrates an example of a proximal end of a therapeutic endoscope with a working channel and lure fittings, in accordance with some embodiments.

FIG. 7, FIG. 8, and FIG. 9 show various examples of the proximal ends of the endoscopes. In some cases, the proximal end of the endoscope can comprise two compartments: a fluid chamber 701 and a dry chamber 702, as shown in FIG. 7. In some embodiments, the fluid chamber can be sealed by means such as o-rings, glue and the like. In some embodiments, the fluid chamber 701 can also be removably coupled to a lure fitting 703 to connect with an external fluid tube. The dry chamber 702 may contain all the electronics, such as electrical board 704 and the components on the board, such as the illuminating LED 705.

FIG. 8 shows another configuration of the proximal end of the endoscope. In this example, a fluid chamber 801 may be reside at the joint between the proximal end and the shaft, and a lure fitting 803 may be coupled to the fluid chamber. The dry chamber 802 of the proximal end only contains electronics 804. In some embodiments, the light source LED 805 may reside in the hand piece and transmit light through the light transmission fiber 807.

FIG. 9 shows an example of the proximal end of a therapeutic endoscope with a working channel. In the example of FIG. 9, the fluid chamber 901 and the dry chamber 902 can be arranged vertically. In some embodiments, a lure fitting 903 for fluid flow may be coupled to the fluid chamber 901. In some embodiments, an instrument lure fitting 906 may be configured to couple to other instruments. In some cases, the working channel 907 may be coupled to the instrument lure 906. In some cases, the working channel 907 can also be connected to the fluid chamber 903 to share the fluid, which allows continuous flow going through the endoscope, such as inflow from the working channel 907, and outflow from the fluid chamber 901.

Interface Between Endoscope and Hand Piece

FIG. 7, FIG. 8, and FIG. 9 also illustrate examples of the interfaces between the endoscopes and the hand pieces. FIG. 7 shows an example of an interface providing mechanical and electrical connection. In the example of FIG. 7, the interface may comprise pins 706 soldered onto the electronics board 704 such as a printed circuit board (PCB). The receptacle connector 707 (e.g., the female connector) is provided on the hand piece. In this case, when the endoscope is plugged into the hand piece, the connection between pins 706 and connectors 707 can not only provide sufficient mechanical connection force between the endoscope and hand piece, but also allow electricity supplied to the endoscope.

FIG. 8 shows another example of an interface between the endoscope and the hand piece, which is mechanical, electrical, and optical for illumination purpose. In this example, the electrical board 804 in the proximal end of the endoscope can be inserted into the receptacle matching connector 806 inside the hand piece. When this connection pair is connected, the bundle of the light transmission fibers 807 at the proximal end of the endoscope can be also aligned with the light source 805 in the hand piece. This interface can provide electrical connection, mechanical connection, as well as alignment of illumination.

FIG. 9 illustrates an example of an interface between a therapeutic endoscope with the hand piece. In this example, the electrical board 904 in the proximal end of the endoscope can be inserted into the receptacle matching connector 908 inside the hand piece. When this connection pair is connected, the bundle of the light transmission fibers 909 is aligned with the light source 905 in the hand piece. This interface can provide electrical connection, mechanical connection, as well as alignment of illumination.

User Control Unit of the Articulation Structure

Figure 10A:
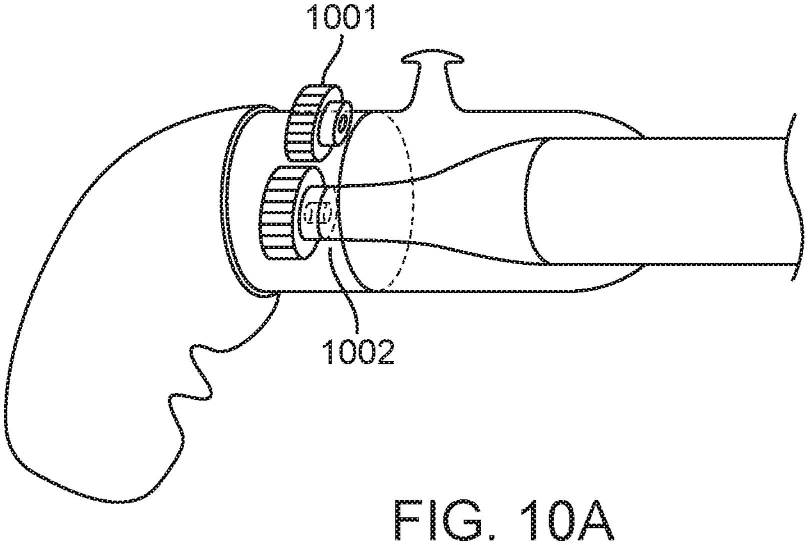
FIG. 10A and FIG. 10B illustrate examples of a proximal end with wire or cable driving configurations to control the distal articulation structures of the endoscopes, in accordance with some embodiments.
Figure 10B:
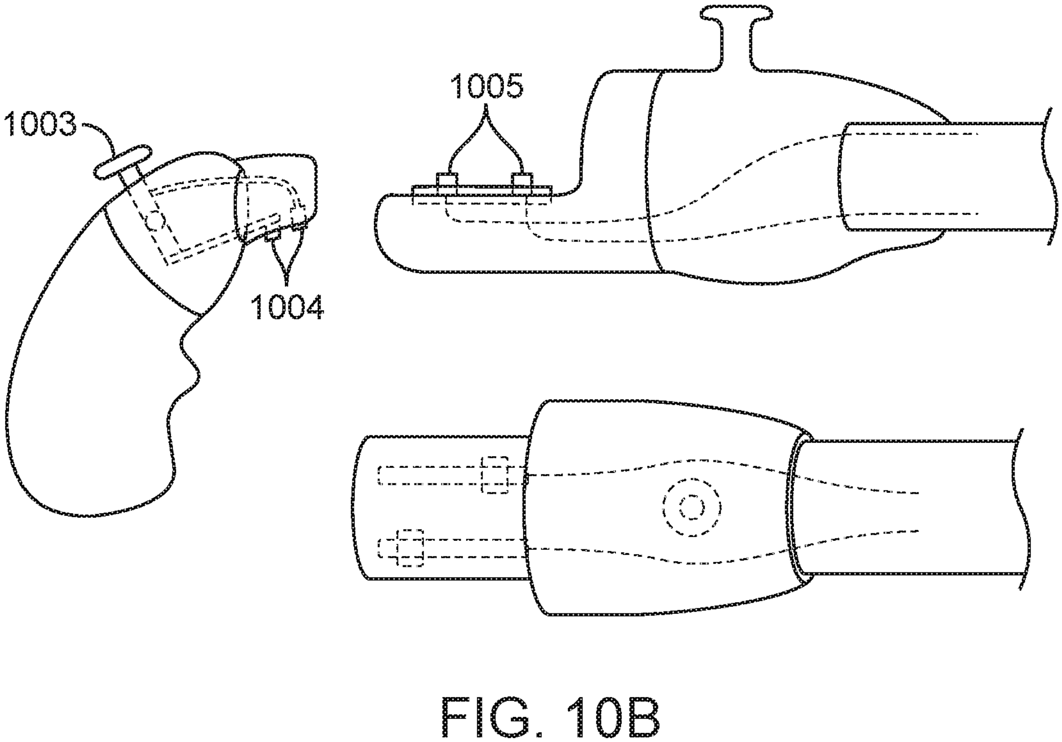

FIG. 10A and FIG. 10B illustrate examples of proximal ends with driving configurations as the user control units to control the articulation structures of the endoscopes. In the example of FIG. 10A, the driving configuration may comprise turning knobs 1001, and the pull wires may be tethered directly to the knob or through another unit, such as gear 1002. When the turning knobs 1001 are rotated by hand, the pull wires may wrap around the inner shaft, which allows the pull wires to be pulled or released. Said driving configuration may reside at the proximal end of the endoscope, or at the hand piece. In some embodiments, only one turning knob is configured to control the articulation structure of the endoscope. In some embodiments, two or more turning knobs may be configured to allow a combination motion to control the articulation structure of the endoscope.

FIG. 10B shows another example of the driving configuration. In the example of FIG. 10B, the driving configuration may comprise a lever 1003 on the hand piece. The lever 1003 may be coupled to two connecting parts 1004, which can further be coupled to the slidable unit 1005 at the proximal end of the endoscope. When the endoscope is coupled to the hand piece, the connecting parts 1004 and the slidable unit 1005 are coupled together. Turning of the lever 1003 may slide the unit 1005 so that to pull and release the pull wires.

In some embodiment, the lever 1003 may reside on the proximal end of the endoscope, and the interface between the endoscope and the hand piece may be proximal to the lever. In this case, the connecting parts 1004 and the slidable unit 1005 are not required. Pull wires can be directly connected to the lever 1003.

In another aspect, provided is an endoscope system comprising the endoscope as described above and a hand piece. In some embodiments, the hand piece of the endoscope system can be re-usable. In some embodiments, the hand piece may be single-use.

Hand Piece and Sterile Drape

Figure 11A:
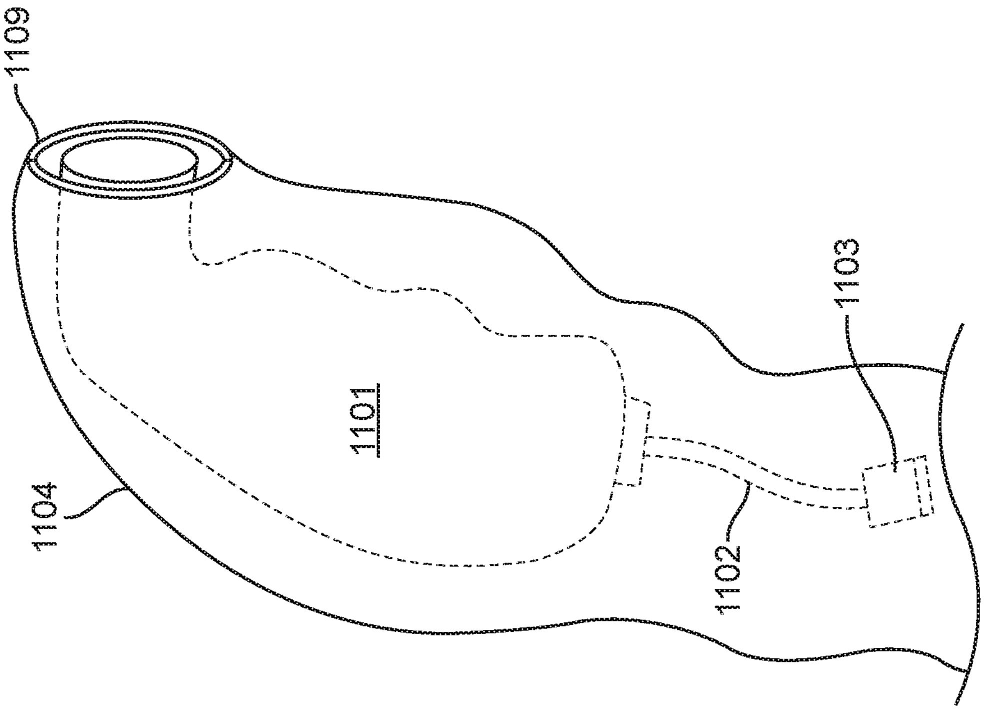
FIG. 11A and FIG. 11B illustrate examples of a hand piece, in accordance with some embodiments.
Figure 11B:
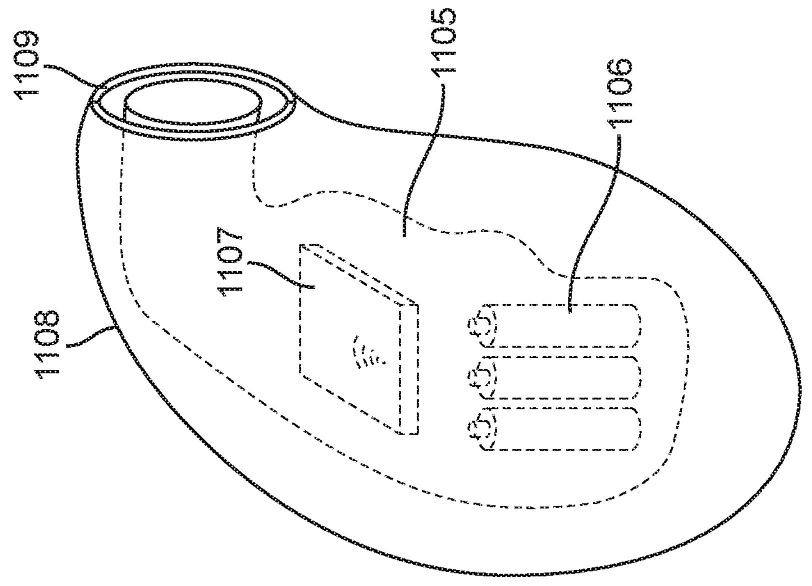

FIG. 11A and FIG. 11B show examples of the hand pieces that may be used in the endoscope system of the present disclosure. In the example of FIG. 11A, the hand piece 1101 comprises a cable 1102 and a cable connector 1103 for connecting with a user interface, such as a computer, a camera control unit, a panel pc, a laptop, a pad and the like. A sterile drape 1104 in the form a sleeve with a connector 1109 at its distal end may be configured to couple with the hand piece 1101 via connector 1109, and cover the hand piece 1101, as well we the cable 1102 and the cable connector 1103.

FIG. 11B shows another example of the hand piece. In this example, the hand piece 1105 may be cable-less, and contain a battery 1106 and a wireless board 1107, such as a WIFI module, a Bluetooth module and the like. In this case, a sterile bag 1108 with a connector 1109 can be used as the sterile drape. In some embodiments, the sterile drape can also be a piece of flexible paper with stick tapes on one side. In this case, the paper can be taped to the hand piece. This design does not require any connector on the drape.

User Interface of the Endoscope System

Figure 12C:
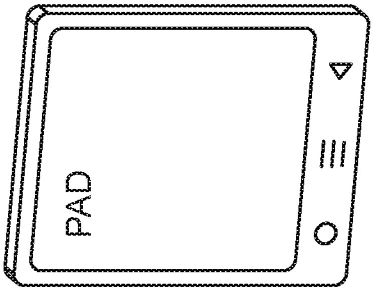
FIGS. 12A-12C illustrates examples of user interfaces which can be used in combination with the endoscope systems of the present disclosure.
Figure 12B:
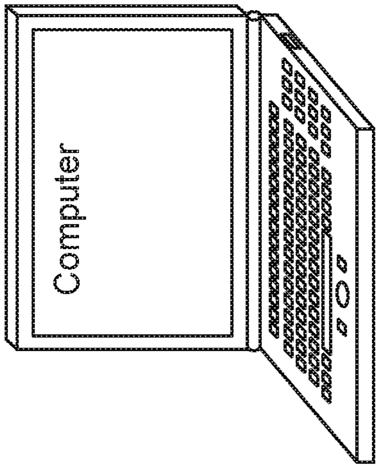
Figure 12A:
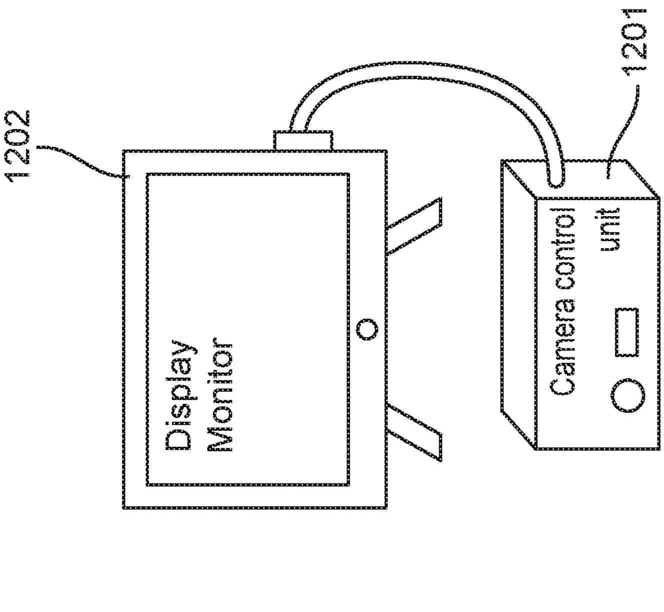

In some embodiments, the endoscope system of the present disclosure is further connected to a user interface, such as a computer, and/or a display. FIG. 12A, FIG. 12B and FIG. 12C show examples of user interfaces which can be used in combination with the endoscope systems of the present disclosure. The user interface may display information related to use of the endoscope such as navigation information, user information (e.g., control parameters), camera view, and the like.

In some embodiments, the user interface may include various devices such as touchscreen monitors, joysticks, keyboards and other interactive devices. In some embodiments, a user may be able to view the camera view provided by the endoscope and provide user input to control one or more functions of the endoscope system. The user input device can have any type user interactive component, such as a button, mouse, joystick, trackball, touchpad, pen, image capturing device, motion capture device, microphone, touchscreen, hand-held wrist gimbals, exoskeletal gloves, or other user interaction system such as virtual reality systems, augmented reality systems and the like.

In the example of FIG. 12A, the user interface comprises a camera control unit 1201 connected to a display monitor 1202. The hand piece of the endoscope system can be connected to the camera control box 1201 to establish system connectivity. FIG. 12B shows a computer user interface. In some embodiments, the computer user interface can be a laptop. In some embodiments, the computer user interface can be a PC. In this case, the hand piece of the endoscope system can be connected to the computer directly through cable or wireless. FIG. 12C shows a pad as the user interface, which the hand piece of the endoscope system can be connected to through cable or wireless.

Port Placement Device

As described above, port placement is currently achieved by conventional laparoscopes designed mainly for the surgical procedure. The laparoscopes have very long shafts which are often very heavy and require enlarge space for operation. Accompanied high-performance cameras with lens are also required, which result in the whole system very expensive. A simple and rapid port placement device with integrated imaging and illumination is in demand.

Figure 14:
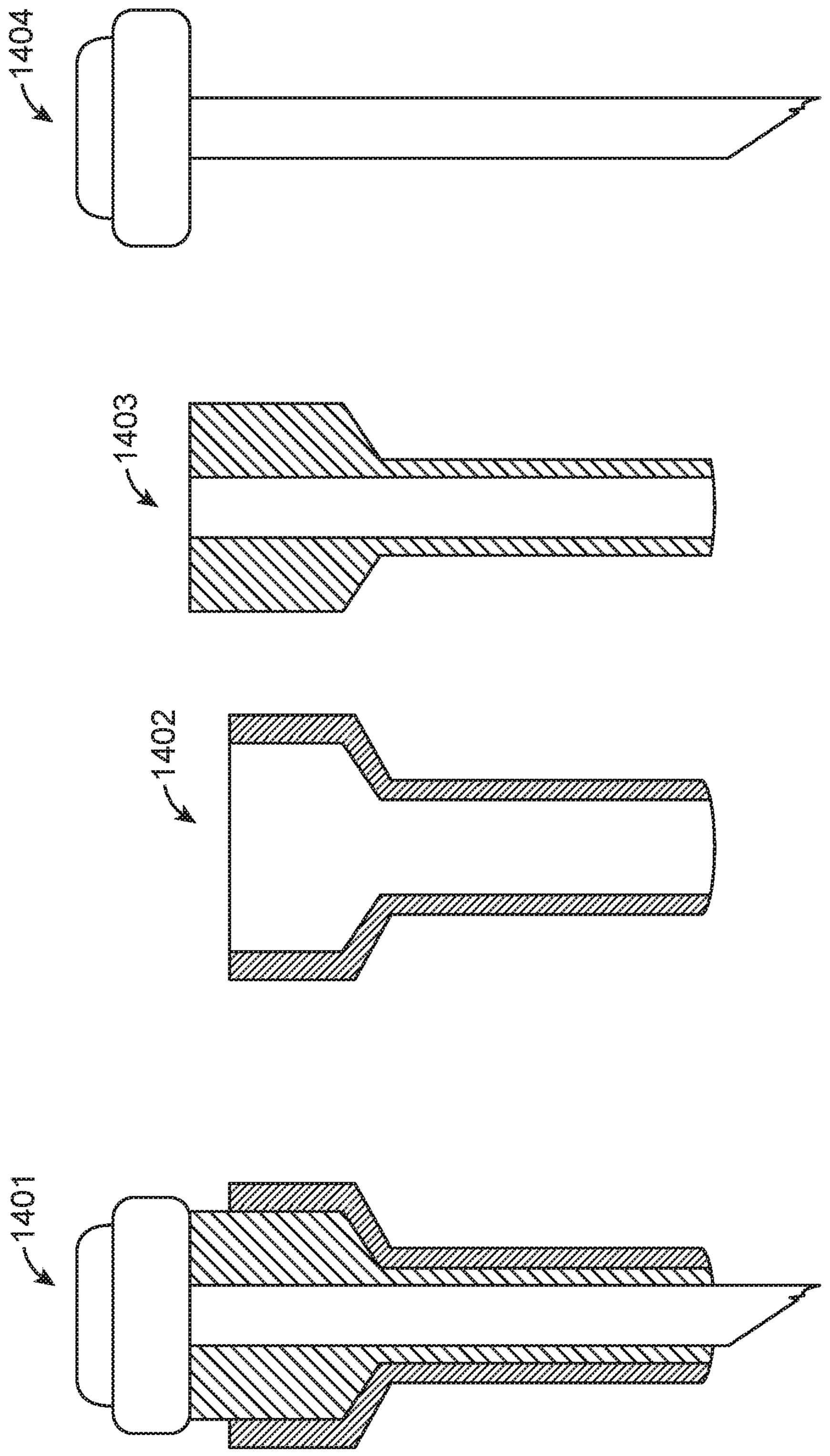
FIG. 14 shows an example of a conventional port placement device with a cannula, an optional cannula adapter, and an obturator.

FIG. 14 shows an example of a conventional port placement device with a cannula 1402, an optional cannula adapter 1403, and an obturator 1401. The cannula 1402 is the unit left at the port on the body wall after port placement. The cannula adapter 1403 is an optional piece which can be inserted into the cannula in order to adjust the size of the port to adapt with the laparoscopic instrument or endoscope. An obturator 1404 can be directly inserted into the cannula as a combined set in the port placement process. In some cases, the obturator can be inserted into the cannula adapter and then into the cannula to create a combined set of three pieces in the port placement process. After port placement, laparoscope can be inserted to observe the inner lumen of the body.

In one aspect, provided herein is a miniaturized low-cost port placement device integrated with imaging and illumination for operations such as laparoscopic and thoracic surgeries and various other applications. In some embodiments, the port placement device may comprise a cannula, a hand piece which can connect with the cannula, an obturator inserted into the cannula, and electrical components such as an imaging device and an illumination element residing at the distal end of the cannula device.

Figure 15:
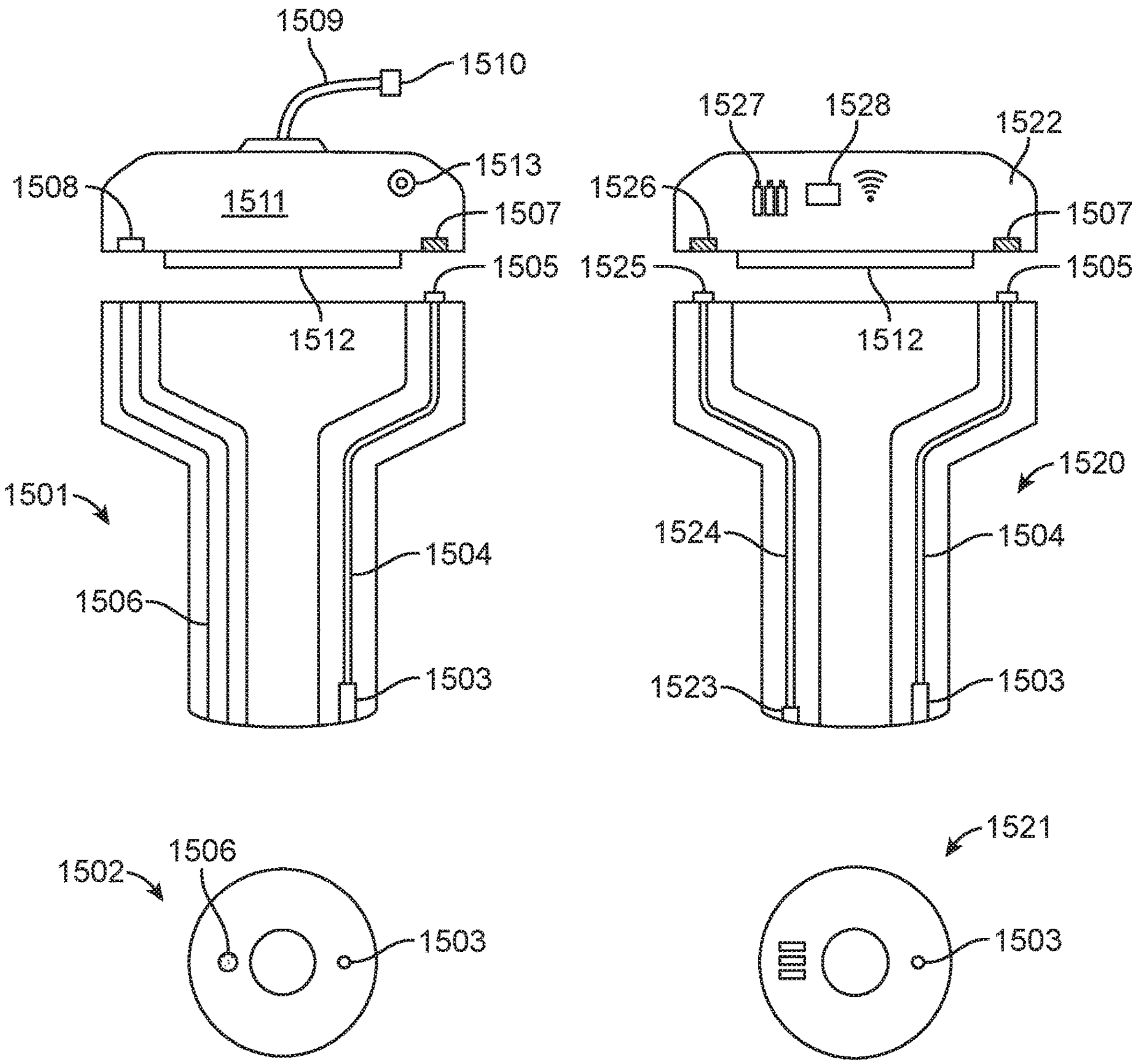
FIG. 15 shows examples of port placement devices with integrated vision and illumination at the distal ends of the cannulas, in accordance with some embodiments.

FIG. 15 shows examples of port placement devices. The port placement devices comprise integrated vision and illumination at the distal ends of the cannulas. The left panel of FIG. 15 shows views of a longitudinal section and cross section of a port placement device. In this case, a camera 1503 may be mounted at distal end of the cannula 1501, and an electrical cable 1504 may be connected to the camera to provide power and/or for data transmission. The camera can be the same as the camera as described elsewhere herein. The electrical cable 1504 may go through the device and connect to a connecting unit 1505 at the proximal end of the cannula. Light transmission fibers 1506 may be used as the illumination element and reside at the distal end of the cannula. Alternatively, the light transmission fibers may reside at the peripheral wall of the cannula. The fibers may run from proximal end to the distal end to transmit light.

In some embodiments, the hand piece 1511 may be removably coupled to the cannula. The electrical unit 1507 configured on the hand piece can connect to the connecting unit 1505 to supply power to the camera, transmit data and control signals. In some embodiments, the hand piece may include control elements such as button 1513 to allow user to control the camera or illumination. For instance, a user may switch the camera on/off, adjust the white balance, perform snapshot, record videos, and/or adjustment strength of illumination via the control elements provided on the hand piece. A light source LED 1508 may be a component of the hand piece. When the hand piece is coupled to the cannula, light can be transmitted from the LED through the light transmission fibers 1506 to the distal end. A mechanical interface 1512 can enable a quick connection between the hand piece 1511 and the cannula 1501. An electrical cable 1509 with a connector 1510 may be configured on the hand piece to connect with a user interface such as a display system.

The right panel of FIG. 15 shows another example of a port placement device of the present disclosure. In this example, the illumination element may be a LED 1523 residing at the distal end of the cannula 1520, and an electrical cable 1524 may be connected to the LED to provide power. The electrical cable 1524 may go through the device and connect to a connecting unit 1525 at the proximal end of the cannula. The hand piece 1522 can be removably coupled to the cannula. An electrical unit 1526 configured on the hand piece can connect to the connecting unit 1525 to supply power to the LED 1523. In some embodiments, the hand piece 1522 may contain a wireless model emitter 1528 and a battery pack 1527. In this case, the cable on the hand piece is eliminated, making the device easier to use and more comfortable to grip by hand. In some embodiments, the battery pack 1527 may be rechargeable. Alternatively, the battery pack 1527 may be disposable.

The camera used in the port placement device can be the same as the camera as described above. For example, the camera may have a dimension (e.g., length, width) of no more than 10 mm. In some embodiments, the camera has a dimension of equal or less than 1 mm. In some embodiment, the camera has a dimension of equal or less than 0.9 mm, 0.8 mm, 0.7 mm, 0.6 mm, 0.5 mm, 0.4 mm, 0.3 mm, 0.2 mm, or 0.1 mm.

The illumination element used in the port placement device can be any illumination element as described above. In some embodiments, the illumination element may have a dimension (e.g., length, width) of equal or less than 1 mm. In some embodiment, the illumination element has a dimension of equal or less than 0.9 mm, 0.8 mm, 0.7 mm, 0.6 mm, 0.5 mm, 0.4 mm, 0.3 mm, 0.2 mm, or 0.1 mm. In some embodiments, the illumination element is one or more LEDs.

In some embodiments, the cannula of the port placement device can be re-usable. In some embodiments, the cannula of the port placement device can be single use. In some embodiments, the hand piece of the port placement device can be re-usable. In some embodiments, the hand piece of the port placement device can be single use.

Figure 16:
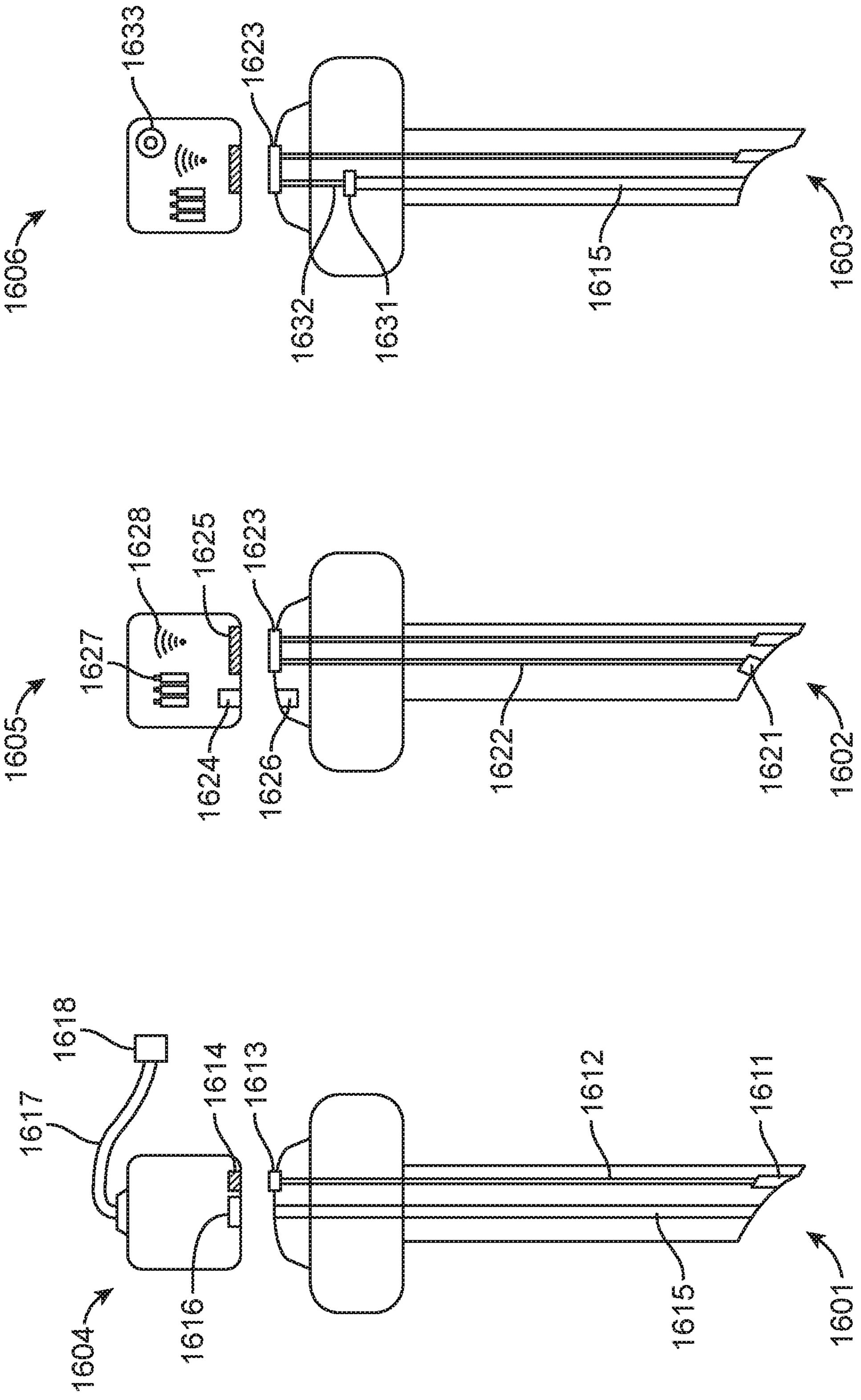
FIG. 16 shows examples of the obturators of the port placement devices with integrated vision and illumination at the distal ends, in accordance with some embodiments.

FIG. 16 shows various examples of port placement devices with integrated vision and illumination at the distal ends of the obturators. In the left panel of FIG. 16, a small camera 1611 can be mounted at the distal end of the obturator 1601, and an electrical cable 1612 may be connected to the camera to provide power and/or for data transmission. The electrical cable 1612 may also connect to connecting unit 1610 at the proximal end of the obturator 1601. Light transmission fibers 1615 may be used as the illumination element and reside next to the camera in the obturator. The fibers may run from proximal end to distal end to transmit light.

In some embodiments, the hand piece 1604 can be removably coupled to the obturator. The electrical unit 1614 configured on the hand piece 1604 can connect to the connecting unit 1603 and supply power to the camera, transmit data and control signals. A light source LED 1616 can be configured as a part of the hand piece. When the hand piece is coupled to the obturator, light can be transmitted from the LED through the light transmission fibers 1615 inside the obturator to the distal end. A mechanical interface may enable a quick connection between the hand piece 1604 and the obturator 1601. An electrical cable 1617 with a connector 1618 may be configured on the hand piece to connect with a user interface such as a display system.

The middle panel of FIG. 16 shows another example of the obturator. In this example, instead of light transmission fibers, the illumination element can be a LED 1621 residing at the distal end of the obturator, and an electrical cable 1622 may be connected to the LED to provide power. The electrical cable 1622 may go through the device and connect to a connecting unit 1623 at the proximal end of the obturator. In some embodiments, the connecting unit 1623 can be a shared connecting unit for both the camera and the LED. When the hand piece is coupled to the obturator, the electrical unit 1625 configured on the hand piece can connect to the connecting unit 1623 to supply power to the LED and the camera. Various interfaces may be used to connect the hand piece and the obturator. In some embodiments, the interface between the hand piece 1605 and the obturator 1602 may be a pair of magnets (1624 and 1626), respectively. In some embodiments, the hand piece 1605 may comprise a wireless model emitter 1628, and a battery pack 1627. In this case, the cable on the hand piece is eliminated, making the device easier to use and more comfortable to grip by hand. In some embodiments, the battery pack 1627 may be rechargeable. Alternatively, the battery pack 1627 may be disposable.

The right panel of FIG. 16 shows another example of the obturator. In this example, light transmission fibers 1615 may reside next to the camera in the obturator. The light transmission fibers can be connected to a light source LED 1631 placed at the proximal portion of the obturator. An electrical cable 1632 may be connected to the LED to supply power. The electrical cable 1632 can be further connected to a connecting unit 1623 at the proximal end of the obturator. This hybrid illumination configuration enables stronger illumination with improved heat management for the LED 1631 because the LED is placed at the proximal end of the obturator where has a larger space as compared to the distal end of the obturator. In some embodiments, buttons 1633 may be configured on the hand piece to allow the user to control the camera or illumination, such as switch the camera on/off, adjust the white balance, perform snapshot, record videos, and/or adjustment strength of illumination.

In some embodiments, the obturator used in the port placement device can be re-usable. In some embodiments, the obturator used in the port placement device can be single-use.

In some embodiments, instead of integrating the imaging device and the illumination element into the obturator, an endoscope with integrated imaging device and illumination element compatible with the inner dimension of the obturator can be used for port placement procedure.

Figure 17:
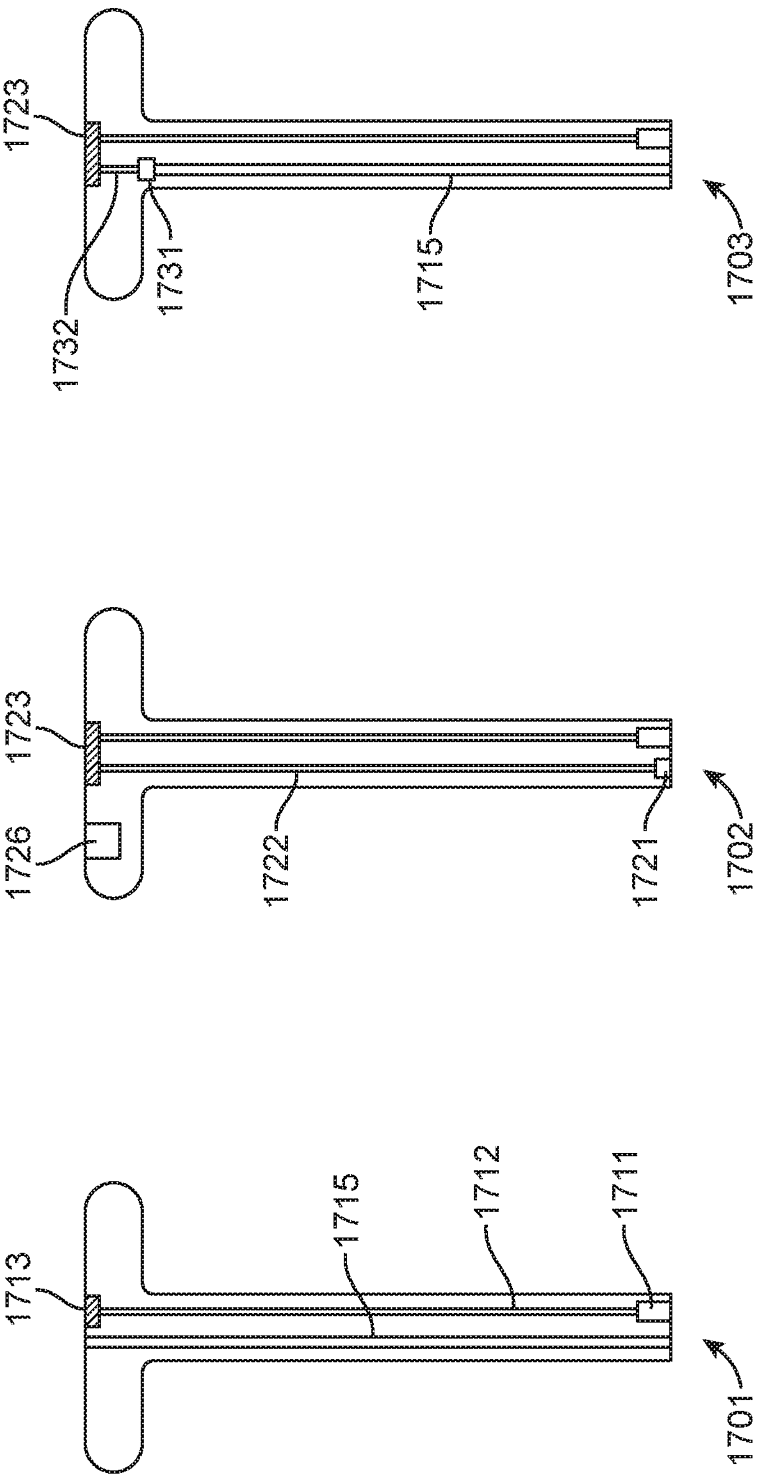
FIG. 17 illustrates examples of endoscopes with integrated vision and illumination at the distal ends, which can be used in combination with the port placement device of the present disclosure, in accordance with some embodiments.

FIG. 17 illustrates examples of endoscopes with integrated vision and illumination at the distal ends, which can be used in combination with the port placement device of the present disclosure. All these endoscopes can be designed to be compatible with the hand pieces as shown in FIG. 16.

In the example of the left panel in FIG. 17, a small camera 1711 can be mounted at distal end of the endoscope 1701, and an electrical cable 1712 may be connected to the camera to provide power and/or for data transmission. The electrical cable 1712 may also connect to connecting unit 1713 at the proximal end of the endoscope. Light transmission fibers 1715 may be used as the illumination element and reside next to the camera 1711. The light transmission fibers may run from the proximal end to the distal end to transmit light.

The middle panel of FIG. 17 shows another example of the endoscope that can be used in the port placement device of the present disclosure. In this example, instead of light transmission fibers, the illumination element can be a LED 1721 residing at the distal end of the endoscope. Electrical cable 1722 may be connected to the LED to provide power. The electrical cable 1722 may also connect to connecting unit 1723 at the proximal end of the endoscope. In some embodiments, the connecting unit 1723 can be a shared connecting unit for both the camera and the LED.

The right panel of FIG. 17 shows another example of the endoscope. In this example, light transmission fibers 1715 may reside next to the camera in the endoscope. The light transmission fibers can be connected to a light source LED 1731 placed at the proximal portion of the endoscope 1703. An electrical cable 1732 may be connected to the LED to supply power. The electrical cable 1732 can be further connected to a connecting unit 1723 at the proximal end of the endoscope. This hybrid illumination configuration enables stronger illumination with improved heat management for the LED 1731 because the LED is placed at the proximal end of the endoscope where has a larger space as compared to the distal end of the obturator.

In some embodiments, the endoscope used in the port placement device can be re-usable. In some embodiments, the endoscope used in the port placement device can be single-use.

The devices as shown in FIG. 15, FIG. 16 and FIG. 17 may simplify the ergonomics during a port placement, because these compact devices have shorter shafts and smaller sizes as compared to the conventional laparoscopes, which may greatly improve the efficiency and safety of the procedure, and shorten time needed.

Sterility Managements of the Port Placement Device

Figure 18:
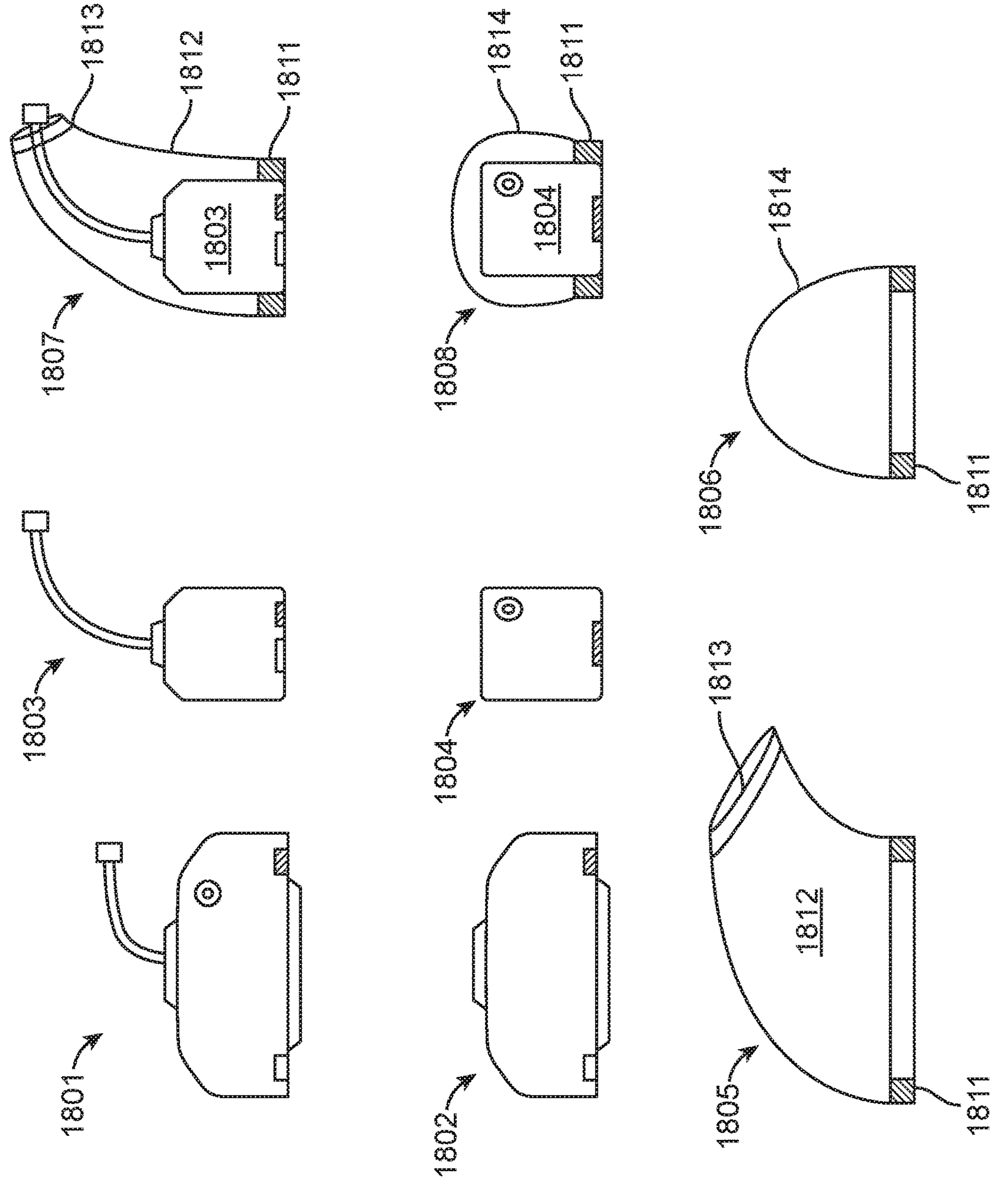
FIG. 18 illustrates examples of sterility managements that can be used on the hand pieces of the present disclosure, in accordance with some embodiments.

To lower the cost of the device, sterility managements are employed to keep the hand piece sterile. FIG. 18 illustrates examples of sterility managements that can be used on the hand pieces of the present disclosure. For the hand piece 1801 and 1803 with cables, a sterile drape sleeve 1805 can be used to cover the hand piece and the cable. In this example, an interface such as the mechanical fitting rings 1811 can be used to attach the sterile drape 1805 to the hand piece. Before port placement, one can insert the hand piece 1803 through the proximal end of the drape sleeve 1813, and snap the distal end of the hand piece to the fitting rings 1811 of the drape. Then roll the sleeve over the hand piece and the cable, so that the drape can fully cover the hand piece 1803 and cable. The term "sterile drape" as used herein refers to a drape used during a surgery to prevent contact with the equipment such as the hand piece and the shaft of the endoscope of the present disclosure.

In some embodiments, hand pieces 1802 and 1804 without cable are used in the port placement devices. In this case, a sterile drape bag 1806 can be provided to cover the hand piece. Before port placement, one can push the hand piece into the sterile drape bag and make sure the fitting rings 1811 of the drape bag fit the hand piece well.

User Interface of the Port Placement Device

Figure 19:
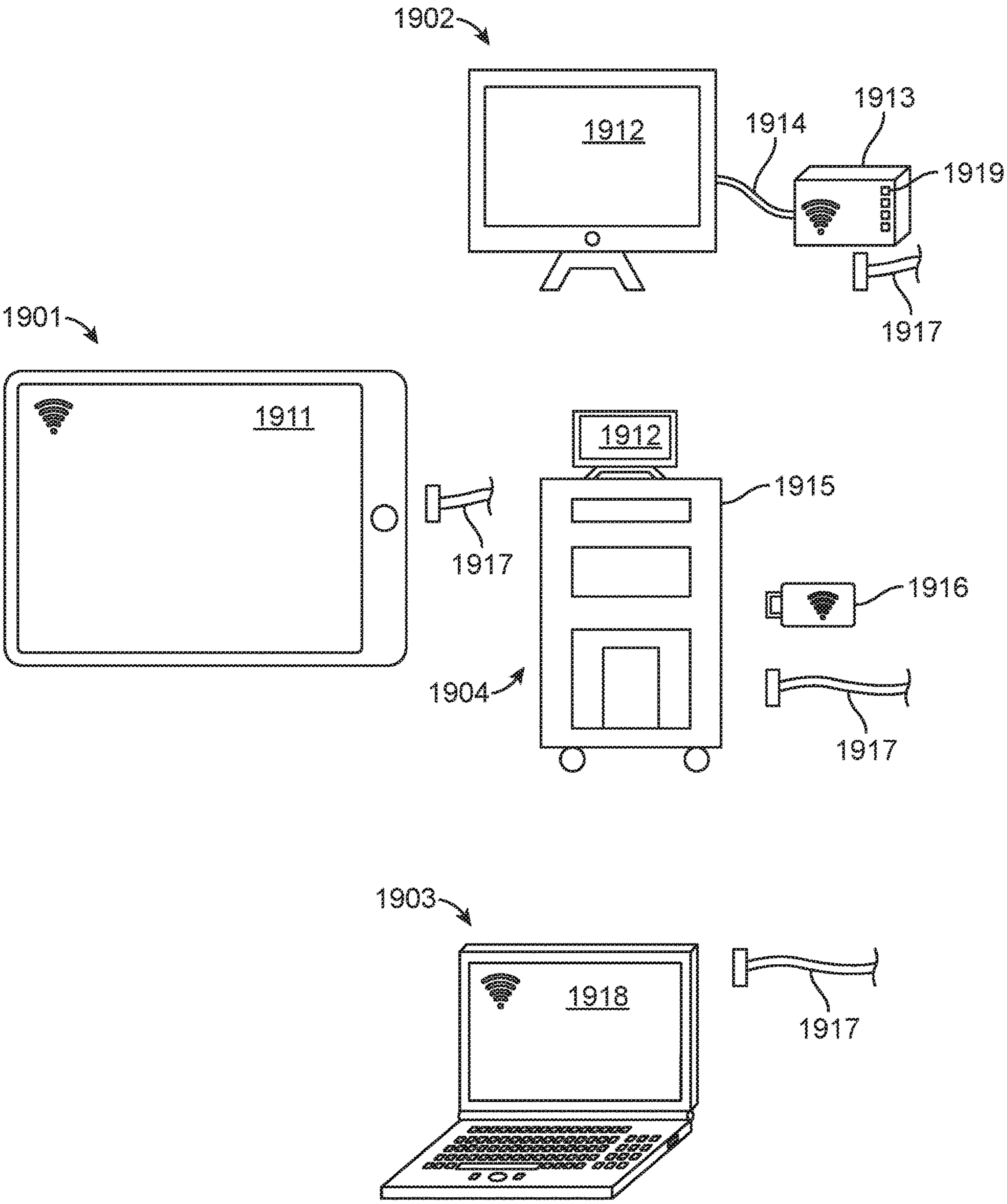
FIG. 19 illustrates examples of user interfaces of the port placement device, in accordance with some embodiments.

FIG. 19 illustrates examples of user interfaces of the port placement device. The user interface provided to the port placement device can be the same as the user interface or user device as described in FIGS. 12A-12C. For example, a computer 1912, a wireless pad (iPad or Android) 1911 or a laptop 1918 may be used to receive the signals from the wireless emitter of the hand piece through WIFI or Bluetooth, and display information such as live videos on the screen. A software can run on the pad to zoom and store images or videos, manage user profiles and patient records, print reports, export data to integrate with hospital patient record system, adjust system setting and the like. In some embodiments, the software also allows user interactions with the view of the endoscope to perform advanced analysis, such as measurements, image analysis and other artificial intelligence related activities.

In some embodiments, a wireless receiver 1913 can be used to receive signals such as image signals from the port placement device through wireless connection, and then send the signals to the display monitor 1912 through the cable 1914. The receiver and the display can be controlled through the buttons 1919 on the receiver 1913.

In some embodiments, a user console may be provided on a computing device mounted to a separate mobile cart 1915. The mobile cart 1915 or external system may be in communication with the port placement device. For instance, images captured by the port placement device may be transmitted to the external system. The communication may be wired or wireless. In some cases, a wireless connection can be achieved through a wireless dongle plugged into the central processing unit of the tower. A receiving software module of the external system may translate the signals and display the information such as images or videos on the monitor 1912.

In some embodiments, all the above-mentioned user interfaces can be connected to the placement device by using a cable 1917. For example, the cable can be used to connect the receiver 1913, the tower system 1915 and the laptop 1918 to the port placement devices.

Figure 20:
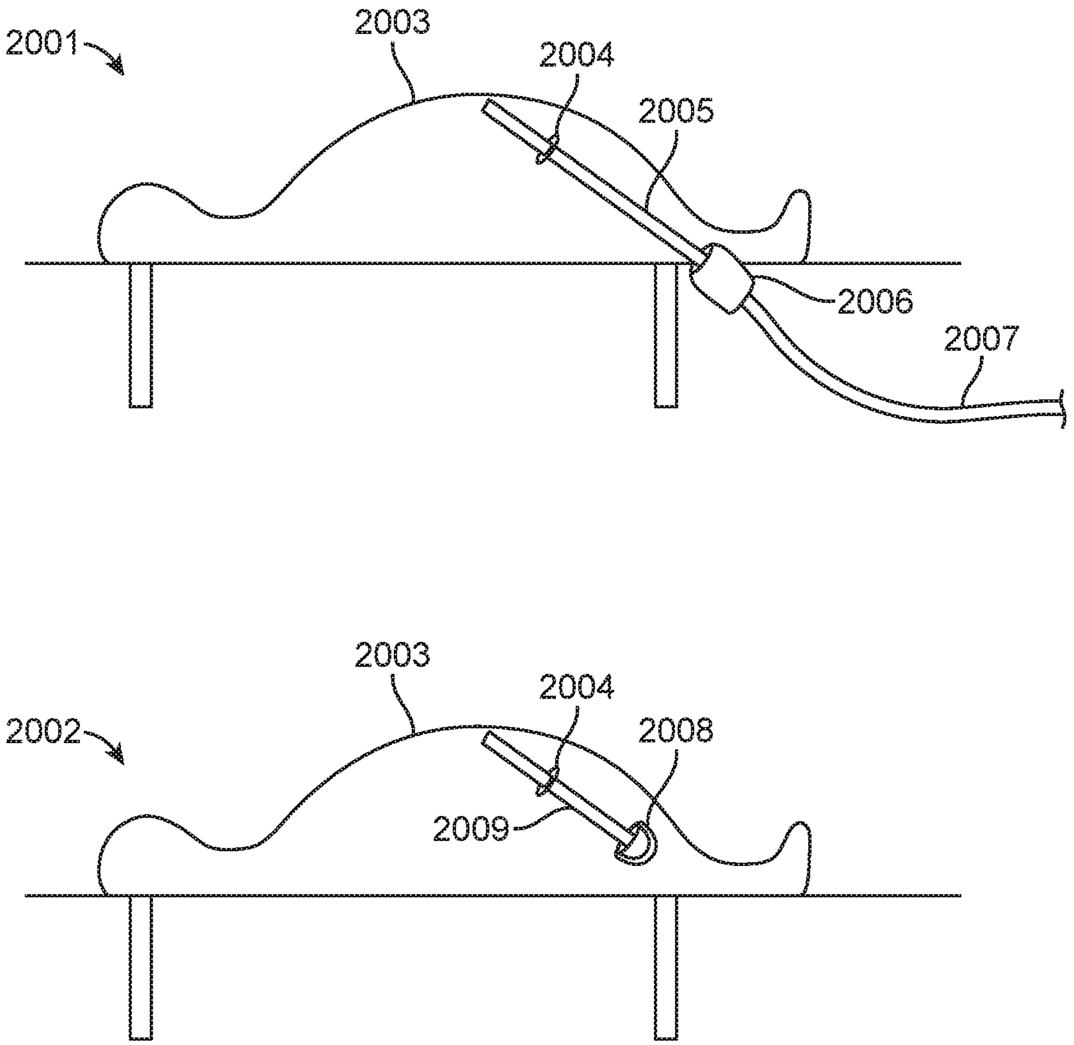
FIG. 20 illustrates operations performed by a conventional laparoscope and the port placement device of the present disclosure in a port placement process.

FIG. 20 shows operations performed by a conventional laparoscope (upper panel) and the port placement device of the present disclosure in a port placement process (lower panel). In the upper panel, the patient abdomen 2003 is insufflated to create a working space inside the patient. While placing the port 2004 on the abdominal wall, the shaft of the classic laparoscope 2005 can take a lot of space around the patient. In addition, the large device with the hand piece 2006 may also be too heavy to operate, and the cable 2007 around the operator can cause the operation even more difficult to perform.

In the lower panel, while placing the port 2004 on the abdominal wall by using the port placement of the present disclosure, the shorter shaft 2009 and the hand piece 2008 with wireless connection make the port placement process easier to perform with a shorter duration, which ensures safety of the patients during the operation.

While preferred embodiments of the present invention have been shown and described herein, it may be obvious to those skilled in the art that such embodiments are provided by way of example only. Numerous variations, changes, and substitutions may now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical port placement device, comprising:

a cannula;

a single-use obturator inserted into the cannula;

a re-usable hand piece removably coupled to the single-use obturator or the surgical port placement device via an interface located at a proximal end of the single-use obturator, wherein the interface simultaneously provides a mechanical quick-release connection via a quick-release mechanism comprising magnets or spring-loaded levers and an electrical connection between the single-use obturator and the re-usable hand piece;

a camera integrated into a distal end of the single-use obturator; and a hybrid illumination component comprising i) a light transmission fiber residing next to the camera inside of the single-use obturator and running from the proximal end to the distal end of the single-use obturator to transmit light from a light source to the camera, and ii) the light source physically disposed on the single-use obturator at the proximal end of the single-use obturator for improved heat management, wherein the camera and the light source of the hybrid illumination component are connected to a power supply and circuit physically disposed on the re-usable hand piece via an electrical connection that is established through the interface when the re-usable hand piece is coupled to the single-use obturator, to provide vision while the single-use obturator is in the cannula during a port placement procedure.

2. The surgical port placement device of claim 1, wherein both the camera and the light transmission fiber reside at the distal end of the single-use obturator and wherein the re-usable hand piece is removably coupled to the single-use obturator.

3. The surgical port placement device of claim 1, wherein the light source is an LED and is located at the proximal end of the single-use obturator that has a space larger than a space of the distal end of the obturator.

4. The surgical port placement device of claim 1, wherein the camera or the light transmission fiber has a diameter of equal or less than 1 mm.

5. The surgical port placement device of claim 1, wherein the light source is one or more LEDs connected to a connection unit at the proximal end of the single-use obturator via an electrical cable.

6. The surgical port placement device of claim 5, wherein the connection unit is configured to provide the electrical connection between the power supply and the circuit located at the re-usable hand piece and the light source thereby allowing a user to control the hybrid illumination component via the re-usable hand piece.

7. The surgical port placement device of claim 1, wherein the re-usable hand piece is connected to a sterile drape via a mechanical interface thereby keeping the re-usable hand piece sterile throughout the port placement procedure.

8. The surgical port placement device of claim 7, wherein the mechanical interface comprises a mechanical fitting ring to attach the sterile drape to the re-usable hand piece.

* * * * *